United States Patent [19]

O'Daly et al.

[11] Patent Number: 5,391,272
[45] Date of Patent: Feb. 21, 1995

[54] ELECTROCHEMICAL IMMUNOASSAY METHODS

[75] Inventors: John P. O'Daly, Carrboro; Robert W. Henkens, Durham; Junguo Zhao; Honghua Zhang, both of Chapel Hill, all of N.C.

[73] Assignee: Andcare, Inc., Durham, N.C.

[21] Appl. No.: 208,146

[22] Filed: Mar. 8, 1994

Related U.S. Application Data

[60] Continuation-in-part of Ser. No. 83,349, Jun. 28, 1993, Pat. No. 5,334,296, which is a division of Ser. No. 846,229, Mar. 6, 1992, Pat. No. 5,225,064.

[51] Int. Cl.$^6$ .............................................. G01N 27/26
[52] U.S. Cl. ............................... 204/153.12; 204/403; 204/418; 435/7.1; 435/7.9; 435/7.93; 435/7.94; 435/288; 435/291; 435/817; 436/501
[58] Field of Search ................. 204/403, 418, 153.12; 435/817, 288, 291, 7.1, 7.9, 7.93, 7.94; 436/501

[56] References Cited

U.S. PATENT DOCUMENTS

| | | | |
|---|---|---|---|
| 4,318,707 | 3/1982 | Litman et al. | 23/230 B |
| 4,340,448 | 7/1982 | Schiller et al. | 204/1 T |
| 4,391,904 | 7/1983 | Litman et al. | 435/7 |
| 4,444,880 | 4/1984 | Tom | 435/7 |
| 4,501,692 | 2/1985 | Gibbons et al. | 260/112 B |
| 4,564,598 | 1/1986 | Briggs | 436/501 |
| 4,663,278 | 5/1987 | DiNello | 435/7 |
| 4,687,735 | 8/1987 | DiNello et al. | 435/7 |
| 4,820,399 | 4/1989 | Senda et al. | 204/403 |
| 4,970,145 | 11/1990 | Bennetto et al. | 435/14 |
| 4,981,785 | 1/1991 | Nayak | 435/7 |
| 5,082,550 | 1/1992 | Rishpon et al. | 204/403 |
| 5,082,786 | 1/1992 | Nakamoto | 435/288 |
| 5,126,034 | 6/1992 | Carter et al. | 204/403 |
| 5,158,869 | 10/1992 | Pouletty et al. | 435/7.9 |
| 5,225,064 | 7/1993 | Henkens et al. | 204/403 |

FOREIGN PATENT DOCUMENTS

WO91/09304  6/1991  WIPO.

OTHER PUBLICATIONS

Albery et al., "Inhibited Enzyme Electrodes. Part 3. A Sensor for Low Levels of H$_2$S and HCN," *Biosensors & Bioelectronics*, 5:397–413, 1990.

Armstrong, Fraser A., "Voltametry of Metal Centres in Proteins," *Perspectives on Bioinorganic Chemistry*, 1:141–165, 1991.

Armstrong, F. A., and Lannon, A. M., "Fast Interfacial Electron Transfer between Cytochrome c Peroxidase and Graphite Electrodes Promoted by Aminoglycosides: Novel Electroenzymic Catalysis of H$_2$O$_2$ Reduction," *J. Am. Chem. Soc.*, 109:7211–7212, 1987.

Rowden, E. F., and Hawkridge, F. M., "Interfacial Electrochemistry of Cytochrome c At Tin Oxide, Indium Oxide, Gold, and Platinum Electrodes," *J. Electroanal. Chem.*, 161:355–376, 1984.

Cass, A. E. G., ed., *Biosensors: A Practical Approach*, Oxford University Press, Oxford/New York, 1990.

Crumbliss, A. L. et al., "Amperometric Glucose Sensor Fabricated from Glucose Oxidase and a Mediator Co-Immobilized on a Colloidal Gold Hydrogel Electrode," Abstract for the ACS North Carolina Divisional Meeting, University of North Carolina at Chapel Hill, Sep. 7–9, 1989, published in USA.

(List continued on next page.)

*Primary Examiner*—John Niebling
*Assistant Examiner*—Bruce F. Bell
*Attorney, Agent, or Firm*—Arnold, White & Durkee

[57] ABSTRACT

An electro-immunosensor which can be used to determine the presence of a wide range of analytes in solution is described. Also described are methods of determining subnanogram levels of analytes in a one-step procedure. This novel immunosensor comprises an analyte binding agent bound to an electrode and a analyte/enzyme conjugate bound to the analyte binding agent as part of a catalytic electrical circuit. Displacement of the conjugate by analyte causes a proportional decrease in current. The immunosensor may also be adapted to detect two analytes in a single step by using different enzymes conjugated to the analyte binding agents.

47 Claims, 21 Drawing Sheets

OTHER PUBLICATIONS

Crumbliss, A. L. et al., "The Use of Inorganic Materials to Control or Maintain Immobilized Enzyme Activity," Symposium on opportunities for inorganic chemistry in biotechnology, Abstract for the ACS National Meeting in Boston, Apr. 23, 1990, published in USA.

Crumbliss, A. L. et., "The Influence of Colloidal Gold Surfaces on Enzyme Activity," Abstract for the ACS North Carolina Divisional Meeting, Sep., 1988, published in USA.

Crumbliss, A. L. et al., "Catalytic and Electroactivity of Irreversibly Adsorbed Enzymes at Gold Electrode Surfaces," Symposium on Protein Electrochemistry: Abstract for the ACS Southeast Regional Meeting (SERM), Oct., 1989, published in USA.

Fair, B. D., and Jamieson, A. M., "Studies of Protein Adsorption on Polystyrene Latex Surfaces," *J. Colloid Interface Sci.*, 77(2):525–534, 1980.

Frew, J. E. et al., "A Method for Estimation of Hydrogen Peroxide Based On Medicated Electron Transfer Reactions of Peroxidases at Electrodes," *Electroanal. Chem.*, 201:1, 1986.

Govindaraju, K. et al., "Active Site Chemistry of Lysyl Oxidase," *J. Inorg. Biochem.*, 29:111, 1987.

Gregg, B. A., and Heller, A., "Cross–Linked Redox Gels containing Glucose Oxidase for Amperometric Biosensor Applications," *Anal. Chem.*, 62:258–263, 1990.

Guo, L-H et al., "Direct Electrochemistry of Proteins and Enzymes," *Adv. Inorg. Chem.*, 36:341–375, 1991.

Guo, L-H et al., "Direct Voltametry of the *Chromatium vinosum* Enzyme, Sulfide: Cytochrome *c* Oxidoreductase (Flavocytochrome *c*552)," *J. Biol. Chem.*, 265(4):1958–1963, 1990.

Guo, L-H et al., "Direct Un-Mediated Electrochemistry of the Enzyme *p*–Cresolmethylhydroxylase," *J. Electroanal. Chem.*, 266:379–396, 1989.

Hagen, W. R., "Direct Electron Transfer of Redox Proteins at the Bare glassy Carbon Electrode," *J. Biochem.*, 182:523–530, 1989.

Hale, P. D., et al., "Amperometric Glucose Biosensors Based on Redox Polymer-Mediated Electron Transfer," *Anal. Chem.*, 63:677–682, 1991.

Henkens, R. W. et al., "Bioactive Electrodes Using Metallo–Proteins Attached to Colloidal Gold," *Rec. Trav. Chem. Pays Bas.*, 106:6–7, 1987.

Henkens, R. W. et al., "Biosensor Electrodes Using Colloidal Gold Supported Oxidase Enzymes," *J. Inorg. Biochem.*, 43:120, 1991.

Henkens, R. W., and O'Daly, J. P., "Multi–Analyte Enzyme Electrodes for Environmental Monitoring," Abstract for the Proceedings of *5th International Biotechnology Conference* in Copenhagen, Jul. 8–13, 1990.

Jönsson, G., and Gorton, L., "An Electrochemical Sensor for Hydrogen Peroxide Based on Peroxidase Adsorbed on a Spectrographic Graphite Electrode," *Electroanalysis*, 1:465–468, 1989.

Kinoshita, Kim, "Carbon: Electrochemical and Physicochemical Properties," John Wiley & Sons, New York, 1988.

Paddock, R. M., and Bowden, E. F., "Electrocatalytic Reduction of Hydrogen Peroxide via Direct Electron Transfer from Pyrolytic Graphite Electrodes to Irreversibly Adsorbed Cytochrome c Peroxidase," *J. Electroanal. Chem.*, 260:487–494, 1989.

Zhao et al., "Direct Electron Transfer at Horseradish Peroxidase–Colloidal Golf Modified Electrodes," *J. Electronanal. Chem.*, 327:109–119, 1992.

Stonehuerner et al., "Comparison of colloidal gold electrode fabrication methods: the preparation of a horseradish peroxidase enzyme electrode," *Biochem. Methods*, 117:208148, 1992.

Aizawa, M., "Principles and applications of electrochemical and optical biosensors," *Analytica Chimica Acta.*, 250:249–256 (1991).

Huet, D. and Bourdillon, C., "Automatic apparatus for heterogeneous enzyme immunoassays based on electrocatalytic detection of the enzyme and electrochemical regeneration of the solid phase," *Analytica Chimica Acta.*, 272:205–212 (1993).

Le Gal La Salle, A. et al., "Utilization of a Nafion-®–modified electrode in a competitive homogeneous electrochemical immunoassay involving a redox cationic labelled hapten–phenytoin," *J. Electroanal. Chem.*, 350:329–335 (1993).

Monroe, D., "Amperometric Immunoassay," *Critical Reviews in Clinical Laboratory Sciences*, 28(1):1–18 (1990).

Monroe, D., "Potentiometric (Bioselective Electrodes) Assay Systems: Utility and Limitations," *Critical Re-*

(List continued on next page.)

OTHER PUBLICATIONS

*views in Clinical Laboratory Sciences,* 27(2):109–158 (1989).

Nakamura, R. M., et al., "Enzyme immunoassays: heterogeneous and homogeneous systems," Handbook of Experimental Immunology in Four Volumes, *vol. 1: Immunochemistry,* Fourth Ed., Chapter 27 (Jan. 1987).

Ngo, T. T., "Immunoassay," *Current Opionion in Biotechnology,* (Reprinted from vol. 2, 1991) 2:102–109 (1991).

O'Daly, J. P., et al., "Electrochemical enzyme immunoassay for detection of toxic substrances," *Enzyme Microb. Technol.,* 14:299–302 (Apr. 1992).

Palmer, D. A., et al., "Flow Injection Electrochemical Enzyme Immunoassay for Theophylline Using a Protein A Immunoreactor and p-Aminophenyl Phosphate-p-Aminophenol as the Detection System," *Analyst,* 117:1679–1682 (1992).

Parra, H. J., et al., "Differential Electroimmunoassay of Human LpA–I Lipoprotein Particles on Ready–to–Use Plates," *Clin. Chem.,* 36(8):1431–1435 (1990).

Roe, R. M., "Enzyme-Linked Immunosorbent Assay of Small Molecular Weight Toxicants," *Revs. in Pesticide Toxicology,* 1:273–287 (1991).

Rosen, I., and Rishpon, J., "Alkaline phosphatase as a label for a heterogeneous immunoelectrochemical sensor," *J. Electroanal. Chem.,* 258-27–39 (1989).

Tie, Feng et al., "An improved ELISA with linear sweep voltametry detection," *J. of Immuno. Methods,* 149:115–120 (1992).

Yim, H. S., et al., "Polymer membrane-based ion-, gas- and bio-selective potentiometric sensors," *Biosensors & Bioelectronics,* 8:1–38 (1993).

ELECTROCHEMICAL IMMUNOASSAY METHODS

BACKGROUND OF THE INVENTION

The United States Government may have certain rights in the present invention under grants from the U.S. Department of Agriculture, Grant No. 93-33610-9605 and the National Institutes of Health, Grant No. 2 R44 HD28884-02 and Grant No. 1 R43 DA07884-01A1.

This application is a continuation-in-part of patent application Ser. No. 08/083,349, filed Jun. 28, 1993, which is a divisional application of U.S. Pat. No. 5,225,064, issued Jul. 6, 1993. The entire text of the above-referenced disclosures are specifically incorporated by reference herein without disclaimer.

FIELD OF THE INVENTION

The invention relates generally to the field of electrochemical immunoassay technology and specifically to enzyme linked electro-immnunosensors, and to methods of using the sensors for small volume determination of subnanomolar levels of analytes that bind to specific antibodies.

DESCRIPTION OF RELATED ART

Immunoassays have typically been used for the detection of antigens or antibodies, less frequently for determination of other classes of compounds. Immunoassays can be generally divided into two types: heterogeneous assays requiring multiple separation steps, and homogeneous assays which are performed directly. Heterogeneous immunoassays in general involve a ligand or antibody immobilized on a solid matrix. The sample containing an analyte is contacted with the immobilized antibody or ligand and the amount of complex formed on the matrix support is determined from a label attached directly or indirectly to the immobilized complex.

Heterogeneous immunoassays may be performed as sandwich assays in which an antigenic molecule is reacted with an immobilized antibody directed to the antigen in a virtually irreversible manner. In a second step, a conjugate formed from the same or different antibody to the antigen and a marker molecule is reacted with the antigen-antibody complex on the immobilization matrix. After removal of excess free marker conjugate, the bound marker conjugate, which is proportional to the amount of analyte in the sample, is measured.

ELISA or enzyme-linked immunosorbent assay is one example of an immunoassay. ELISAs are extensively used in biotechnology applications, particularly as immunoassays for a wide range of antigenic substances. The sensitivity of ELISA is based on the enzymatic amplification of the signal. However, despite such widespread use, ELISA has several disadvantages, including inconvenience and expense that preclude general use. Several washing steps may often be required in ELISA procedures to remove excess antibody not bound to the immobilization support or to remove excess analyte or antibody following the primary binding reaction. A separate wash may be necessary to remove excess enzyme-conjugate that does not bind to the immobilized antibody-analyte complex. Multiple wash steps are time-consuming, and require either increased handling or added automation steps and reagents, thereby significantly increasing assay time and cost.

There has been some effort to provide semi-automation of ELISA, for example the apparatus and method described in U.S. Pat. No. 4,981,785. However, although immunochemical assays are suitable for detecting several types of analytes, e.g., trace levels of agricultural chemicals (Jung, et al, 1989), these assays generally require laboratory preparation by highly trained personnel, and expensive automation. Additionally, while immunoassays are adaptable to different formats, these assays have not proved rugged and simple enough for on-site analysis.

Unfortunately, alternative analytical methods for quantitative determination of trace amounts of many compounds, such as hazardous agricultural chemicals or metabolites produced in vivo, typically involve relatively complex and inconvenient procedures. In most cases, samples must be collected, extracted and prepared for specific analyses. For example, in commonly used gas chromatographic analysis, aqueous samples are extracted with an appropriate organic solvent, evaporated to dryness, and finally, redissolved in an appropriate solvent (Ramsteiner, et al., 1974). Similar extraction procedures are required for gas liquid chromatographic analyses (Muir, 1980). However, these methods lack the sensitivity, reliability and ease required for determination of trace amounts of chemical compounds.

Recent advances in biotechnology, specifically the advent of monoclonal antibodies and the use of enzyme labels in place of radiolabels, have promoted a rapid expansion of immunoassay applications to toxic chemicals (Collins, 1985; Gould and Marx, 1988; Stanker, 1989; Watkins, 1989; Roberts, 1989). Other labels besides radio labels may be employed for detection in immunoassays. Enzyme labels, for example, are particularly useful because the catalytic properties of the enzyme provide powerful biochemical amplification, thereby allowing detection of extremely low analyte concentrations.

An enzyme multiplied immunoassay technique has also been applied to the determination of several different drug species. In this system a hapten-enzyme conjugate is prepared so that enzyme activity is retained after conjugation. When the conjugate binds with the hapten-specific antibody there is a loss in enzyme activity. Any free hapten (drug) in a sample reduces the inhibition by competing for antibody binding sites. Enzyme activity is thus proportional to concentration of free hapten. This type of assay has been developed by the Syva Company (Palo Alto, Calif.) under the trademark EMIT. However, the EMIT assay is less satisfactory for detection of relatively large molecules such as proteins. This may be due to binding of the specific antibody to a cryptic epitope thereby preventing the drug mediated release of the enzyme.

One example of the progress of immunodetection technology is the analysis of the environmental waste by-product Atrazine. The atrazine studies are exemplary of the state-of-the-art and are used as an example to illustrate the inherent drawbacks in the art of analyte detection. In 1985, Huber reported the development of a solid phase enzyme immunoassay for the rapid determination of atrazine in fresh water. The method was reported to measure atrazine in the 1.1 to 2200 ppb range. EIA sensitivity was further improved by using spheres as antibody carriers and by using affinity purified antibodies.

In 1988, Bushway, et al. described an improved immunoassay for determining atrazine in water and soil which was adaptable to field testing. The method was indicated to be useful for screening with fairly good accuracy when compared to high performance liquid chromatography. The particular immunoassay reported was claimed to show a linear relationship between 0.5 ppb and 10 ppb. A similar immunoassay has been described for analyzing atrazine in food (Bushway, et al. 1989). A variety of solid and liquid foods were tested including corn, pineapple, nuts, milk, fruit juices, and several types of colas. However, as mentioned earlier, these immunoassays require extensive time periods for incubations and may involve multiple washing steps.

The reliability of commercial enzyme immunoassay in determining atrazine in water has been reviewed by Fleeker and Cook (1991). Samples from several locations were tested for triazine herbicides employing a commercial enzyme immunoassay and gas chromatography. The limit of detection for EIA was 0.4 ppb. Similar types of comparison by Goolsby, et al. (1991) suggested that immunoassay might be the basis for development of a rapid, reliable and inexpensive screening tool for triazine herbicides in water.

Finally, trace levels of atrazine in drinking water have been detected using a piezo electric immunobiosensor (Guilbault 1992). The piezo electric immunobiosensor system is based on changes in the diffraction of light due to the deposition of molecules on the electrode surface. The change in the refractive index is measured electronically. Although having a detection limit of 0.03 to 100 ppb atrazine, the system has several shortcomings, foremost of which is a required incubation period for the antibody to absorb sufficient atrazine to provide a detectable signal. Furthermore, the system requires continuous calibration, expensive electronics and highly skilled technicians. Thus, the advantages of the high sensitivity of the piezo electric immunobiosensor are offset by the disadvantages of slow response, expense, and the requirement for incubation and washing steps.

Present electrochemical immunoassay systems have been generally divided into potentiometric and amperometric depending on the electric output measured. In a recent review, Monroe (1990) described the state-of-the-art of electro biosensors. Current technology measures a range of analytes that is predicated by the reactants, the availability of specific field-effect-transistors (FET), and the reaction conditions, such as pH and oxidation. Furthermore, the sensitivity of the electrodes to adverse assay conditions, and therefore the variability of the signal greatly limit their widespread use and demands highly skilled technicians and equipment to attain consistent results. Present immunobiosensors combine the specificity of antibodies with gas selective electrode (GSE) for measuring the production of an enzymatic by-product. However, this system requires multiple steps (i.e., a heterogenous assay), and relies on accommodating assay conditions, and is therefore impractical for a wide range of sample types such as tissue samples and environmental sampling. These constraints limit the samples that can be tested, the ease of testing, and also greatly increase the expense.

There remains an important need to develop rapid, simple and reliable tests for determining trace amounts of different classes of materials, including molecular entities such as trace elements, simple inorganic and organic chemicals, and complex macromolecules such as nucleic acids, carbohydrates, lipids, proteins and combinations thereof. Furthermore, a means of simple, reliable and rapid on-site testing is needed to detect such molecules in remote or non-institutional locations in the field, in small clinics, doctors' offices, or even in the home. Some useful applications might include testing blood and urine samples for drugs or toxic substances, or testing of foodstuffs for environmental chemicals by relatively unskilled personnel.

Likewise, a simple, rapid, and inexpensive molecular detection system would greatly benefit developing countries that may lack access to the sophisticated equipment, facilities and trained personnel necessary for traditional testing methods. Finally, methods are needed to detect trace levels of small compounds, so that effective, point source detection of environmental pollutants and areas of contamination can be more easily identified.

SUMMARY OF THE INVENTION

The present invention seeks to overcome these and other drawbacks inherent in the prior art by providing a novel electro-immunosensor which is convenient, sensitive and can be applied to a one-step electrochemical determination of a wide range of analytes. In addition the system can be adapted to measure dual analytes in a single process. Particular advantages of the invention are that it can be applied in non-laboratory settings by nonprofessionals to achieve fast and accurate determinations of a variety of compounds.

Generally, the invention concerns an electro-immunosensor comprising an electrode on which is deposited colloidal gold adsorbed anti-analyte antibody reversibly bound to an enzyme-analyte conjugate. The electrode may be any inert conducting material such as carbon, gold, silver, platinum, etc. Prior to adsorption of the anti-analyte antibody on colloidal gold, it is usually desirable to coat the colloidal gold with a protein, e.g. bovine serum albumin or Protein A. In certain embodiments, two or more anti-analyte antibodies may be adsorbed to colloidal gold and deposited on the electrode surface. The enzyme is selected to provide a catalytic current when properly set up in an electrochemical cell in the presence of a suitable substrate. For example, horseradish peroxidase bound to a selected analyte and adsorbed onto the electrode surface-deposited anti-analyte antibody will generate a measurable current in the presence of hydrogen peroxide. When a sample containing analyte is then added, the analyte displaces the enzyme/analyte conjugate. The enzyme is no longer in close contact with the electrode surface so that electron transfer cannot occur. One observes a decrease in catalytic current and this decrease is proportional to the amount of enzyme/analyte conjugate displaced from the surface bound anti-analyte antibody.

In a more particular embodiment, the electro-immunosensor comprises an electrode onto which surface is deposited an anti-analyte antibody bound to protein-coated colloidal gold. A second anti-analyte antibody is also bound to the protein-coated colloidal gold deposited on the electrode surface. Preferably, the first anti-analyte antibody is specific for an analyte different from and non cross-reactive with the second anti-analyte antibody.

The present invention also includes methods of using the electrochemical enzyme-linked immunoassay comprising incubating the novel electro-immunosensor with a sample suspected of containing an analyte one desires to measure. The electrode will be suitable coupled with a reference electrode for measuring amperometric current. Where a peroxidase is employed as the enzyme, for example horseradish peroxidase, the enzyme substrate $H_2O_2$ is added. The analyte causes a decrease in catalytic current and the decrease is related to the level of analyte present in the sample. In preferred embodiments, a mediator which enhances electron transfer between the immobilized peroxidase and the electrode surface is included. The mediator may be free in solution or immobilized on the electrode surface. The concentration of the mediator may be in the range of 0.2 mM–2 mM.

The invention is readily adaptable to the determination of two analytes. This is achieved by the adsorption of separate anti-analyte antibodies to the colloidal gold and binding the appropriate analyte/enzyme conjugate to each of the antibodies. A different enzyme is used for each conjugate so that the two analytes can be differentiated in a single step assay. In certain preferred embodiments one may employ horseradish peroxidase and glucose oxidase as the enzymes. Enzyme conjugates may be prepared, for example, from two different hormones. Leuteining hormone and follicle stimulating hormone may be measured employing this system. Other analytes, not necessarily limited to polypeptide hormones, may be determined in a similar manner using the appropriate antibodies. While enzymes other than HRP and GOD may be utilized, the inventors have found that good results are obtained with HRP and GOD.

As used in the context of the present invention, analyte is defined as a species which interacts with a non-identical molecule to form a tightly bound, stable complex. For practical purposes, the binding affinity is usually greater than about $10^6 M^{-1}$ and is preferably in the range of $10^9–10^{15} M^{-1}$. The analyte may be any of several classes of molecules, including biological molecules such as proteins, lipids, saccharides, nucleic acids and combinations thereof. The method of the present invention is also useful for detecting sulfur, oxygen and nitrogen heterocyclics as well as alicyclic hydrocarbons, polynuclear aromatics and a wide range of halogenated compounds. Examples include benzenoids, polynuclear hydrocarbons, nitrogen heterocyclics, sulfur heterocyclics, oxygen heterocyclics, and alkane, alkene and alkyne hydrocarbons. In specific exemplary embodiments, the analyte may be a nitrogen heterocyclic such as a triazine, and more specifically atrazine. The analyte could also be any of a number of polypeptides including hormones such as follicle stimulating hormone or luteinizing hormone. Of course it will be understood that these are by way of example only and that the invention is applicable to detecting an extraordinarily wide range of compounds.

In general, one will select enzymes that efficiently catalyze electron transfer or redox reactions. Examples of enzymes that may be used in these assays include horseradish peroxidase (HRP), catalase, glucose oxidase (GOD), cholesterol oxidase, xanthine oxidase (XO) and similar enzymes. One will usually desire to add an electron transfer mediator such as ferrocene and its derivatives or other compounds with similar function such as phenazines, phenoxazines and benzoquinones.

In order to effect electron transfer, a suitable substrate for the enzyme must be present. For horseradish peroxidase this is $H_2O_2$ at a concentration of between about 0.2 and about 0.8 mM.

Yet another embodiment of the invention is a method for preparing an electrochemical immunoassay sensor for determining femptogram levels of an immunogenic analyte employing the following steps: immobilizing on colloidal gold an antibody which specifically reacts with an analyte; depositing the immobilized antibody on an electrode surface; separately immobilizing a peroxidase conjugate on colloidal gold wherein the peroxidase conjugate is formed from a peroxidase enzyme and the analyte; and incubating the peroxidase conjugate with the electrode surface-deposited antibody to form an antibody peroxidase conjugate complex.

A particular advantage of the present invention is the ability to detect analytes in samples ranging from animal tumors to environmental samples; examples include pesticide residues, drugs, drug metabolites, toxins, poisons, proteins, peptides, etc. This list is not all-inclusive and it will be recognized by those of skill in the art that virtually any organic compound may be detected by the disclosed electrochemical immunoassay technique, provided a suitable binding molecule is available. More specifically, it will be apparent that numerous compounds may be identified and detected using the described methods, and that it is particularly useful for detecting residual concentrations of virtually any molecule to which an appropriate antibody or binding moiety may be directed.

Generally, one will desire to prepare an antibody, antisera or binding entity to the analyte or group of analytes one wishes to detect. It is understood that the analyte binding molecule of this invention can be mono- or polyvalent. Antibodies are used here as an example since they are well characterized and understood to be specialized proteins composed of sequences of amino acids formed three-dimensionally into specific shapes, allowing specific binding of particular proteins. The bound moieties are known as antigens and fit to the antibodies much as a key in a lock or hand in a glove. The binding entity need not necessarily be limited to proteins and may be another type of macromolecule whether naturally occurring, recombinant or synthetic, e.g., a synthetic receptor, a carbohydrate/protein complex or nonprotein moiety, to which a ligand or cross-reacting compound binds. The binding entity may, for example, be an organic or inorganic chelator or even a modified binding material such as a molecular sieve, diatomaceous earth or liposome, provided the analyte is selectively and reversibly bound.

Antibody-antigen binding includes the interaction with molecules that are, by themselves non-antigenic, that is, molecules that do not intrinsically elicit an immune response. This class of compounds, known collectively as haptens, are generally small molecules and include a wide range of inorganic and organic compounds. As used in the context of this invention it will be apparent to those skilled and versed in the art that an analyte or analytes include molecules that may not be immunogenic, but are antigenic, and are therefore a hapten. Antibody responses to molecules that are heterocyclic in nature are also within the spirit and scope of this invention.

To prepare antibodies that are specifically directed to a small molecule or hapten, one prepares an immunogen comprising a hapten-carrier complex, i.e., attaches the small molecule to a carrier which will stimulate an immune reaction. Typically, the hapten-carrier complex is injected into an animal, e.g., a rabbit, and the polyclonal antibodies produced by the animal are isolated from a blood sample. Furthermore, it will be apparent to those of skill in the art that monoclonal antibodies can be attained that interact specifically with the hapten molecule. It will be apparent to those skilled in the art that there are multiple means of deriving polyclonal and monoclonal antibodies with sufficient specificity and affinity to a wide range of analytes. All immunoglobulins derived for use in an electro-immunosensor system are deemed to be within the spirit, scope and concept of the invention.

DETAILED DESCRIPTION OF PREFERRED EMBODIMENTS

Figure 1:
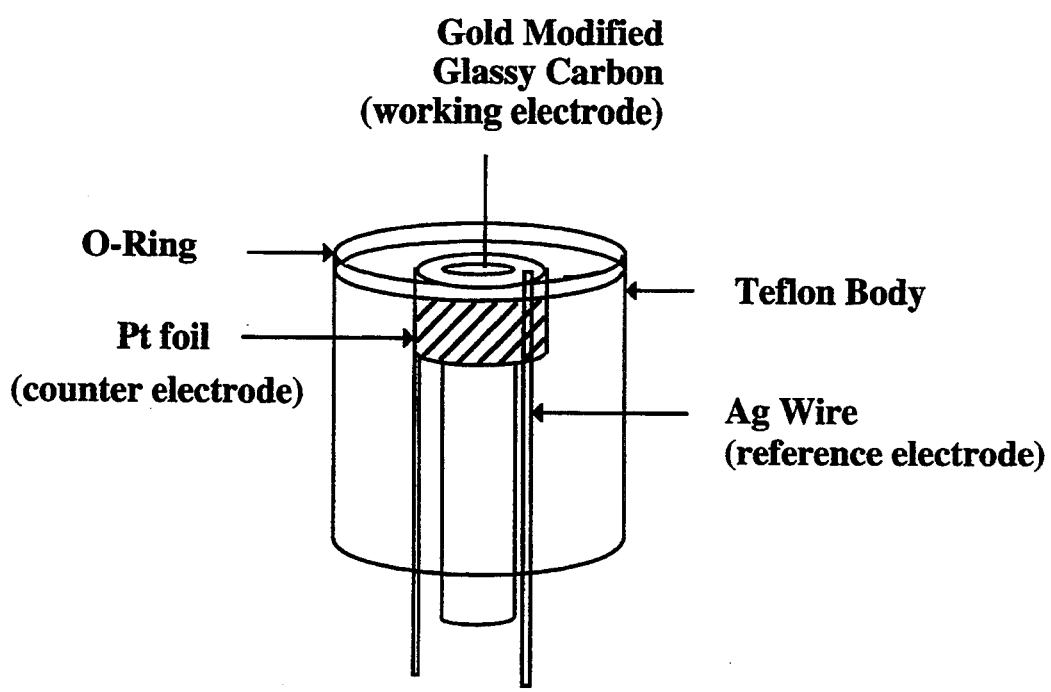
FIG. 1 shows a typical microcell electro-immunosensor configuration. The cell consists of a planar three-electrode microcell suitable for samples of 20 μl–5 ml. The working electrode is a glassy carbon rod surrounded by Teflon insulation which is wrapped with a platinum foil counter electrode. A silver wire tip emerges from the insulation to provide a reference electrode and all three electrodes are held together by a teflon body.

The present invention provides a novel electro-immunosensor and methods for using the electro-immunosensor to detect the presence of trace amounts of various molecules or chemical compounds. A particular advantage of the present invention over traditional methods is its applicability to a wide variety of circumstances without the need for highly trained specialists. For example, the devices and methods of the present invention will allow relatively unskilled persons in non-laboratory settings to perform accurate determinations of the levels of specific analytes.

In its most general sense, the invention comprises an electrode to which is bonded a receptor molecule which will bind an analyte with some specificity. In most cases the receptor molecule is an antibody that immunoreacts with the analyte. The electrode is further prepared by binding to the immobilized receptor, and the analyte conjugated to an enzyme which transfers electrons, such as an oxidase. When suitably combined with a reference and working electrode, the electrode/receptor/analyte/enzyme complex in the presence of a substrate for the enzyme causes a measurable electrical current.

An aspect of the invention is a method of using the electrode described in the previous paragraph to detect the presence of an analyte in solution. The invention may also be adapted to determine the presence of two analytes simultaneously. In these methods, the electrode is brought into contact with a solution suspected of containing the analyte. If the analyte is present in the solution, it will displace some of the analyte/enzyme which is bound to the receptor molecule. When this occurs, the current will decrease in inverse proportion to the level of analyte in the solution. The effect may be enhanced by the addition of a mediator which is an electron donor/acceptor which will amplify the reaction.

Amplification in this sense and as employed herein is intended to define the numerous product molecules resulting from a single enzyme-labeled antibody reacting with the enzyme substrate molecule. Electrode chemical redox enzyme immunoassay technology takes advantage of the selectivity of antibody reactions, the amplification of enzymes, and the ease with which small amounts of material may be detected electrochemically (Eggers et al., 1982; Wehmeyer, 1985; Halsall et al., 1988). Very little sample is required (on the order of 10 $\mu$l) enabling routine determination of analyte levels on the order of $10^{-14}$ moles (Jenkins et al., 1987). Redox enzyme amplification occurs because a single redox enzyme-labeled antibody recognition results in shuttling of large numbers of electrons between the enzyme and the electrode.

Preparation of Antibodies

It may become necessary in the practice of the invention to produce antibodies to particular analytes for which antibodies are not commercially available. Antibodies, both polyclonal and monoclonal, specific for an analyte may be prepared using conventional immunization techniques, as will be generally known to those of skill in the art. A composition containing antigenic epitopes of the analyte, or the entire analyte can be used to immunize one or more experimental animals, such as a rabbit or mouse, which will then proceed to produce specific antibodies against the analyte or analytes. Polyclonal antisera may be obtained, after allowing time for antibody generation, simply by bleeding the animal and preparing serum samples from the whole blood.

To obtain monoclonal antibodies, one would also initially immunize an experimental animal, e.g., a mouse, with an antigenic analyte composition. One would then, after a period of time sufficient to allow antibody generation, obtain a population of spleen or lymph cells from the animal. The spleen or lymph cells can then be fused with immortal cell lines, such as human or mouse myeloma strains, to produce antibody-secreting hybridomas. These hybridomas may be isolated to obtain individual clones which can then be screened for production of antibody to the desired analyte or analytes.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against the analyte(s). Hybridomas which produce monoclonal antibodies to the selected antigens are identified using standard techniques, such as ELISA and/or Western blot methods. Hybridoma clones can then be cultured in liquid media and the culture supernatants purified to provide the analyte-specific monoclonal antibodies.

Enzyme Immunoassays

Antibodies often provide highly specific recognition of a particular compound or molecule and are widely used in detection and purification methods. In the present invention, this specificity of binding is combined with the sensitivity of electrochemical reactions to provide the surprising ability to detect trace amounts of analytes. Some less sensitive methods are based on enzyme immunoassays. Enzyme immunoassays (EIAs) are quantitative methods in which an antigen antibody reaction is determined by enzyme measurements. EIA methods are generally classified as heterogenous or homogenous. In heterogenous EIA methods, the antigen-antibody interaction does not affect the activity of the enzyme label. On the other hand, in homogenous EIA, the antigen-antibody interaction modulates the activity of the enzyme. Because of the modulation of enzyme activity, a separation step is not required.

In contrast, heterogenous EIA assays require a separation step. A particularly well known example of a heterogenous EIA is the enzyme linked immunosorbent assay (ELISA). ELISA has been used in several modifications that typically include a reactant immobilized onto a solid phase matrix. ELISAs exhibit high sensitivity because of the enzymatic nature of the read-out, and the specificity of the reactants. In heterogenous EIA systems the enzyme on the labeled antigen or antibody retains enzymatic activity after reaction with the reciprocal antibody or antigen. EIAs are similar to RIAs, except that in EIAs enzymatic activity is measured instead of radioactivity. The choice of separation phase in heterogenous EIAs is limited by the size of the enzyme label. In ELISA, the enzymatic activity in the bound or free fraction is typically quantified by enzyme catalyzed conversion of a relatively colorless or nonfluorescent substrate to a highly colored or fluorescent product which may be measured spectrophotometrically.

ELISA assays may be further classified as competitive or noncompetitive. In competitive ELISA an antigen-enzyme conjugate is utilized and specific antibody is immobilized on a solid surface. Assay steps generally include: 1) physical adsorption or covalent attachment of a specific antibody to a matrix; 2) removal of excess unattached antibody by a washing procedure; 3) incubation of the immobilized antibody with the enzyme labeled antigen and standard or sample antigen until the antibody-antigen reaction has proceeded to equilibrium, followed by washing with a buffer containing a wetting agent after; 4) incubation of the solid phase with the enzyme substrate in an appropriate buffer; and 5) stopping the enzyme reaction and measuring substrate reaction product. In this type of assay, substrate product concentrations are inversely proportional to the concentrations in the standard or test antigen. Competitive ELISA may also be conducted using antibody enzyme conjugates. With this modification antigen is attached to a solid phase. Binding of enzyme labeled antibody to the solid phase antigen is competitively decreased by adding a standard or unknown test antigen.

Noncompetitive ELISA techniques are an example of type I "reagent observed" or excess antibody assays. In these methods the analyte or antigent is reacted with a stoichiometric excess of antibody and the extent of the antigen-antibody interaction is measured in a second step. There are some advantages to this type of assay using labeled antibody including: 1) pure analyte does not have to be isolated; 2) a separation step usually eliminates unwanted sample interference before reaction with specific enzyme label antibody; 3) assay procedure requires less reaction time than competitive ELISA; and 4) the sensitivity may be increased over comparable competitive ELISA assays.

EIA methods commonly employ solid phase immobilization of antigen or antibody. This is typically obtained by covalent binding or by adsorption through noncovalent interactions. Bead-like particles have also been used for immobilization, including polystyrene, polyacrylamide and magnetite. Plastic microtiter plates as immobilization surfaces have become increasingly popular.

The amount of immobilized antigen or antibody on the matrix surface is important because high concentrations tend to reduce specific binding and enhance nonspecific binding, whereas at low concentration there is little specific binding capacity and assay sensitivity is lowered. Nonspécific adsorption onto the solid phase can be reduced by including a nonionic detergent such as Tween-20 in the buffer medium. Alternatively, proteins such as gelatin or bovine serum albumin may also be employed for this purpose.

There are certain limitations and disadvantages to heterogenous EIA. For example, nonspecific absorption may significantly affect measurement of extremely small concentrations of analyte. The extent of the antigen-antibody interaction may also be a limiting factor in the assay. Finally, there is the prozone or "high-dose hook" effect. This may lead to reduced reactivity when high levels of analyte are present. Sensitivity of these assays may be increased by the use of highly specific monoclonal antibodies. This is especially true where it is found that mixtures of certain monoclonal antibodies increase the avidity of the reaction by binding in a cooperative manner to form tightly bound complexes with the antigen.

A particular advantage of the present invention is that it is no longer necessary to carry out the many steps and washes involved in these immunoassay techniques, thus saving valuable time. In addition, the present invention can be adapted to be used in the field, or in clinical settings wherein the necessary laboratory equipment and personnel needed to perform these assays is not readily available.

Homogenous Immunoassays

Homogenous immunoassays may be carried out without separation of the free and bound antibody components. These assays are based upon antibody mediated changes in enzyme activity. Assays are thus performed by simply mixing the sample with the reagents and measuring the resulting enzymatic activity which correlates with the concentration of the analyte. Homogenous EIAs have been used for assays of drugs and hormones; however, such assays are generally considered to be less sensitive than heterogenous EIAs, and possible interference in the sample components must be taken into consideration.

Radioimmunoassay

Radioimmunoassay (RIA) is well known detection technique. RIA employs a specific antibody to bind a radiolabeled analyte standard. In the absence of unlabeled analyte the radioactivity count is maximized and represents zero analyte detection. When unlabeled analyte is added to the system by sample addition, a competitive binding reaction between the free analyte and antibody bound labeled component takes place and a certain fraction of radiolabeled analyte will be displaced. The amount of displacement is proportional to the concentration of free analyte added. Equilibrium is allowed to occur and unbound radiolabeled analyte is removed by washing. Subsequently a radioactivity measurement is made and the decrease in radioactivity can be taken as a measure of the concentration of free analyte in the sample.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

PREPARATION OF COLLOIDAL GOLD ADSORBED ENZYMES

This example describes the preparation of colloidal gold solutions, the absorption of enzyme to the colloidal gold and the deposition of the colloidal gold absorbed enzyme onto the electrode surface by a simple evaporation procedure. Colloidal gold biosensor electrodes have been previously described in U.S. Pat. No. 5,217,594, the entire specification of which is herein incorporated by reference. These electrodes employ colloidal gold adsorbed enzymes deposited on the electrode surface and, in some cases, a carrageenan polymer at the surface of the electrode. The colloidal gold provides a biocompatible surface on which a biologically active enzyme may be placed by simple absorption. Enzyme adsorbed colloidal gold may be readily deposited onto any suitable electrode material such as carbon, platinum, or gold, thereby providing a layer of biologically active material on the electrode surface.

If desired, the surface-deposited immobilized enzyme may then be coated with a compatible polymer such as carrageenan. This serves to stabilize the enzyme and provides a macroporous layer which allows ready access to the supporting electrolyte buffer components, electroactive mediator and other compounds in the solution.

Colloidal Gold Solutions

Gold trichloride (Fisher Chemical Company, St. Louis, Mo.) was used to prepare colloidal gold solution with a particle diameter of approximately 300Å by the method of Mormans, et al, (1985). A solution of 1% aqueous sodium citrate was added to a rapidly boiling, stirred solution of gold trichloride, and the solution was refluxed for 30 minutes. The final concentrations (weight percent) were 0.01% $HAuCl_4$ and 0.03% sodium citrate.

Horseradish Peroxidase Adsorbed to Colloidal Gold

Horseradish peroxidase (HRP) type VI-A (Product #P6782, Sigma Chemical Company, St. Louis, Mo.), activity equal to 1000 units per mg solid was dialyzed against 2 mM sodium phosphate at pH 7.0. One unit is defined as oxidizing 1 μmole 2,2'-azino-bis (3-ethylbenzthiazoline-6-sulfonic acid) (ABTS) per min.

A colloidal gold solution prepared as described was concentrated to about 5–10 mg Au/ml by centrifugation at room temperature at 9,000 X g for 30 minutes. The concentrated solution was added drop-wise to a stirred solution of horseradish peroxidase (HRP) in water (1–10 mg HRP/ml) on ice. The final ratio of HRP to gold added was approximately 100 mg HRP per gram gold.

HRP immobilized on colloidal gold retained full enzymatic activity. Activity was determined in a spectrophotometric assay with 2,2'-azino-bis (3-ethylbenzthiazoline-6-sulfonic acid) (ABTS) as a secondary substrate (Zhao, et al, 1992). The assay mixture contained 2 mM ABTS, 1 mM of $H_2O_2$, approximately $3 \times 10^{-10}$M HRP, and 50 mM sodium citrate at pH 4.5. Spectrophotometric analysis was performed at 405 nm.

Deposition of HRP on Electrode Surface

Figure 2:
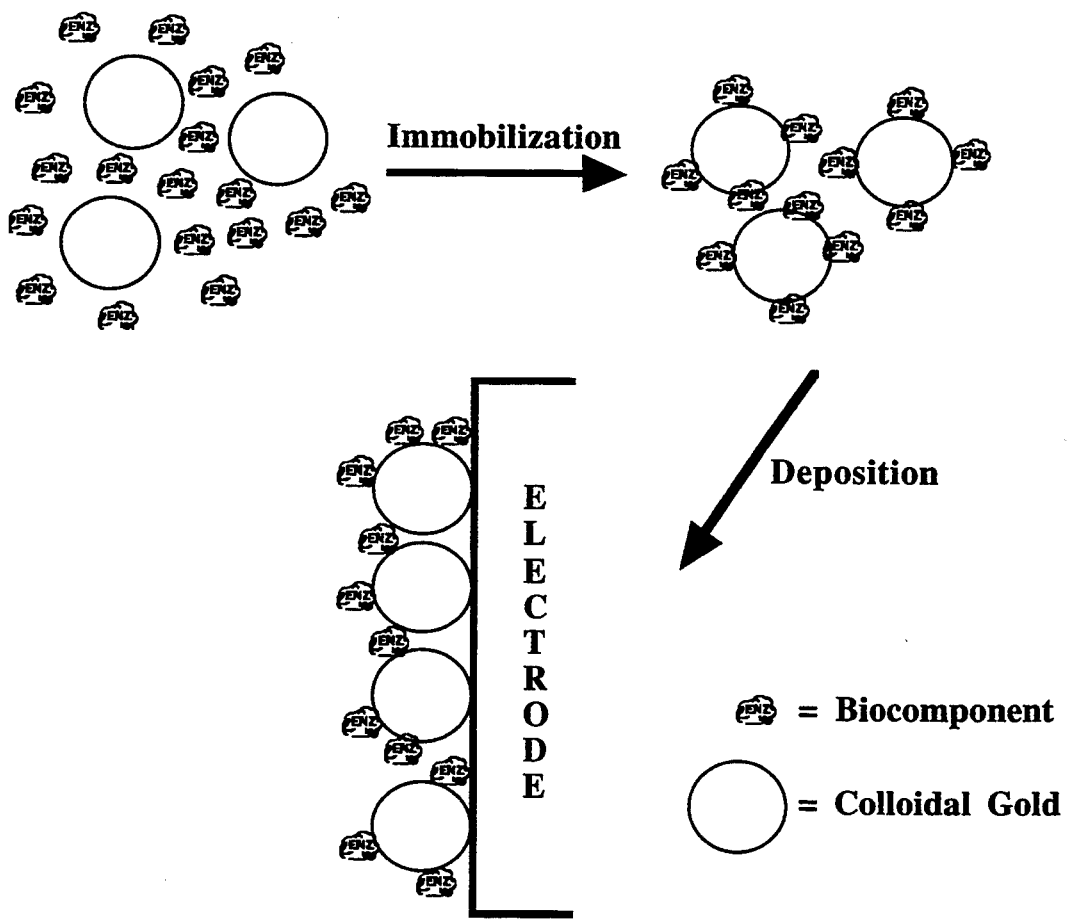
FIG. 2 is an illustration showing immobilization of an enzyme on colloidal gold surface and deposition of the gold-immobilized enzyme onto an electrode surface.

Deposition of colloidal gold immobilized HRP on the electrode surface was accomplished by evaporating 3 μl of HRP colloidal gold solution onto a glassy carbon working electrode of a cell configured as shown in FIG. 1. This produced about a monolayer of colloidal gold-HRP coating on glassy carbon that was stable under operational conditions. An illustration showing enzyme immobilization and deposition on the electrode surface is shown in FIG. 2.

HRP deposited on the electrode surface retained electrocatalytic activity. Activity of the deposited HRP was determined by detecting the catalytic current produced in the presence of $H_2O_2$ and an electron transfer mediator. The buffer solution was 50 mM phosphate at pH 7 containing 10 mM NaCl. No deaeration was necessary in most cases. Ferrocene carboxylic acid was used as a mediator at a fixed concentration of 0.2 mM which is well into the region where the electrode response is independent of mediator concentration.

A Pine instrument RD4 bi-potentiostat interfaced to an IBM 486 computer was used for electrochemical measurements. The system was controlled with ASYST programs and electrochemical data were collected directly and processed in the computer. Cyclic voltammograms were obtained in quiescent solution. In steady state amperometry experiments, the potential was set at 0 volts (Ag) in stirred buffer and the steady state current was measured. In the absence of HRP, the electrodes had no significant response to $H_2O_2$ (up to 2 mM) in steady state amperometry measurements at 0 volt (Ag).

EXAMPLE 2

FERROCENE-ATRAZINE CONJUGATES AS ELECTRON TRANSFER MEDIATORS

Increasingly, undesirable chemicals are released into the environment as a result of manufacturing processes, waste disposal and agricultural activity. Agriculture, for example, has become dependent on a wide range of herbicides and pesticides to increase yields and protect crops. Unfortunately, the chemicals themselves or their breakdown products leach into the soil, finding their way into water supplies and eventually into the food chain. The ideal solution would be to prevent pollution at the source; however, often a first consideration is a test to determine the presence of an undesirable compound.

Of particular concern are commonly used pesticides such as Dichlorovos, Phosphamidon, Diazoanon, or Parathion and herbicides such as Basta, Herbiace, Gleen, Dalapon, bromoxynil or Roundup and compositions containing bialaphos, phosphinothricin, (N-(phosphonomethyl)glycine) and sulfonylurea. These organic compounds typically contain heteroatoms and often are resistant to breakdown, persisting for long periods of time. Many compounds are found only in trace amounts in soil or water, yet exposure to even these low amounts over long periods may have serious effects on human health.

Atrazine, a triazine herbicide, is an example of a widely used pesticide that is sold worldwide (Bushway, et al, 1989; Guilbault, et al, 1992). This herbicide is the second most widely used pesticide in the United States with approximately 70 million pounds of active ingredient being applied each year (Bushway, et al, 1988). Atrazine is a pre- or post-emergent annual grass and broad leaf weed control agent for corn, sorghum, sugar cane, macadamia, and pineapple. Although it is approved for use on only five agricultural products, livestock as well as other crops are exposed to atrazine by mechanisms such as wind drift, soil rotation erosion, water contamination, etc.

The well-known persistence of triazines in fresh water is documented in several aquatic outdoor studies (Peichl, et al, 1984; Huber, 1985). Municipal, private and agricultural water sources are susceptible to contamination in areas of frequent atrazine use. In soil, atrazine carryover may be injurious to certain rotational crops (Farris and Haigh, 1987). There is thus an urgent need to monitor water sources, soil samples and feed and drinking water provided to farm animals and products for human consumption.

This example shows that when an organic compound ("analyte") is bound to an electron transfer mediator, the electron transfer properties of the mediator are substantially unaffected. Specifically, the example is illustrated with ferrocene carboxylic acid covalently bound to atrazine, but the same effect may be obtained with other mediators covalently attached to an analyte. Covalent bonds may be formed, for example by carbodiimide reaction between carboxyl of the acid group of ferrocene carboxylic acid and the amine functions on atrazine.

Synthesis of Ferrocene-Atrazine Conjugate

Figure 3:
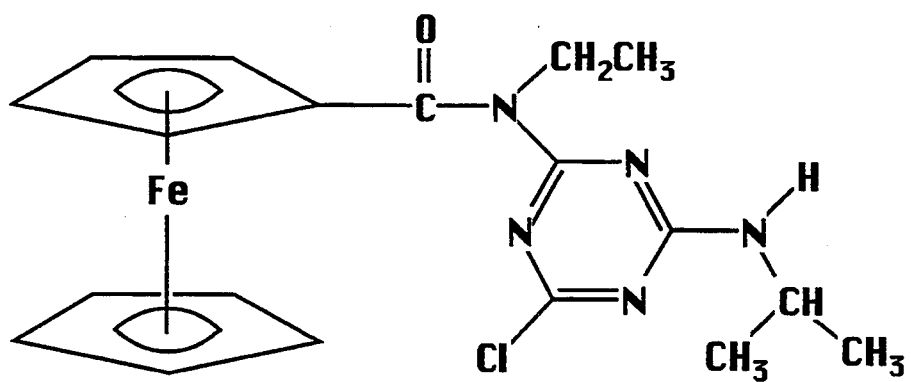
FIG. 3 shows the structure of a ferrocene-atrazine conjugate where the two molecules are covalently bound.

A mediator analyte conjugate was synthesized by reacting ferrocene carboxylic acid with atrazine in the presence of the coupling reagent dicyclohexylcarbodiimide (DCC). This procedure mimics standard carboxamide formation in peptide syntheses. The desired carboxamide was formed in 23.3% yield on a 0.5 mM scale. The carboxamide was remarkably stable and was purified by flash chromatography. The product was characterized by NMR. The structure is shown in FIG. 3.

The ferrocene atrazine conjugate was isolated and tested as an electron transfer mediator. The testing protocol employed was as described in Example 1. The ferrocene atrazine conjugate mediated the production of a catalytic current in a manner similar to free ferrocene.

Figure 4:
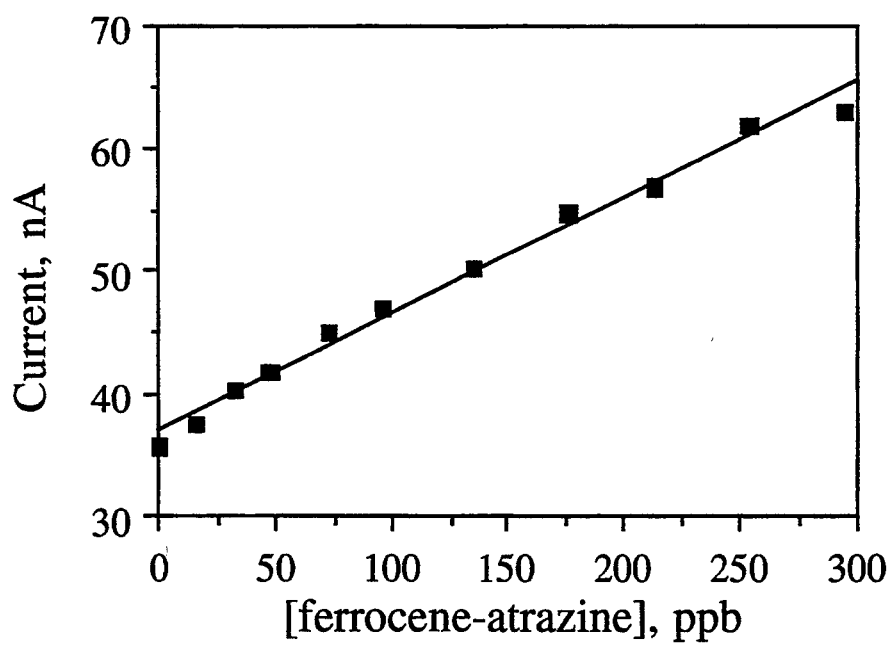
FIG. 4 is a plot of current change in varying concentrations of ferrocene-atrazine complex. The background electrolyte is 50 mM phosphate, pH 7.0 in 10 mM NaCl with 0.5 mM $H_2O_2$ as substrate. The plot is uncorrected for background current.

The concentration of the ferrocene atrazine conjugate was varied in order to establish a range of response for this mediator (FIG. 4). Catalytic current was measured over a range of 0–300 ppb in 50 mM phosphate, pH 7.0 with 10 mM NaCl, with the substrate ($H_2O_2$) at a concentration of 0.5 mM. Under these conditions, the action of the ferrocene atrazine conjugate as an electron transfer agent was not distinguishable from the background current below about 10–20 ppb, indicating a limitation on the levels of detection.

EXAMPLE 3

DETECTION OF ε-2,4-DNP-L-LYSINE BY INCREASED CATALYTIC CURRENT

Enzymes and antibodies immobilized on colloidal gold offer an important new route to amperometric biosensor electrodes. Such electrodes overcome typical problems encountered with commercial clinical biosensors including instability, slow response, and interference caused by lack of direct efficient coupling between the enzyme and the transducer. As discussed above however, one disadvantage of this method is that the response signal is dependent on the concentration of the mediator.

The mediator in this example, ferrocene monocarboxylic acid showed similar redox electrochemistry before and after conjugation with the antigent analyte as demonstrated in cyclic voltametry. The response signal of the HRP electrodes depended on the concentration of both $H_2O_2$ (enzyme substrate) and the ferrocene antigent conjugate (electron transfer mediator between HRP and the conductive electrode surface). At a fixed $H_2O_2$ concentration well above the saturation point for $H_2O_2$, the signal was linearly proportional to ferrocene antigent conjugate concentration at low concentrations and leveled off at higher concentrations of greater than 20 μM.

Figure 10:
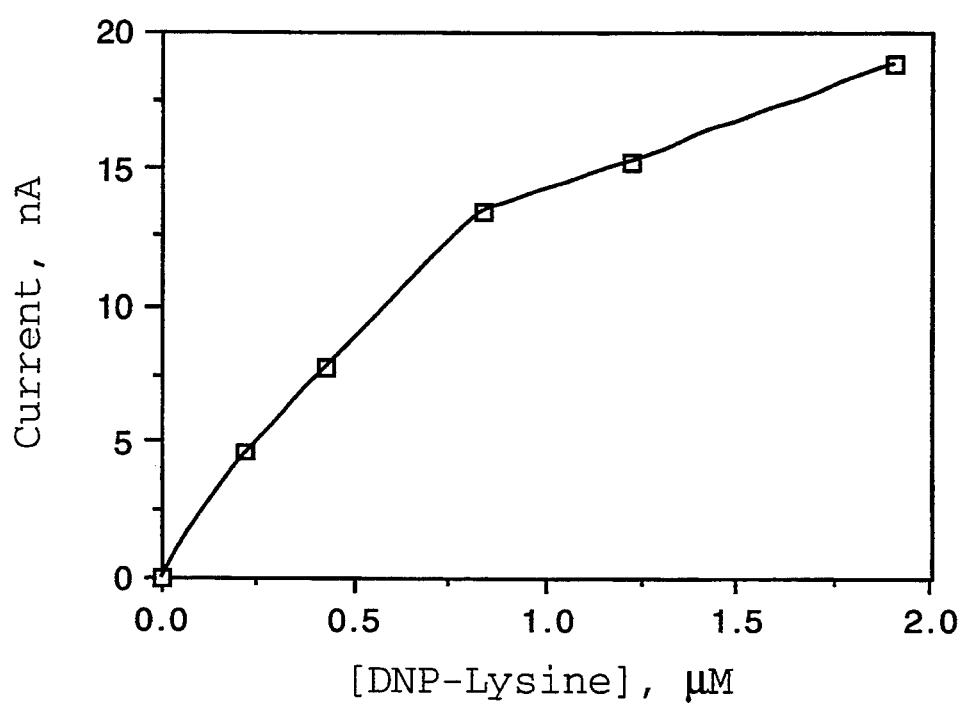
FIG. 10 shows a catalytic current plot with a planar three electrode microcell with a $H_2O_2$ concentration of 10 mM, antibody at 2.0 nM, Mediator ε-,2,4-DNP-L-lysine at 1.25 mM. The background electrolyte is 0.05M potassium phosphate buffer, pH 7.0. Corrections have been made to eliminate background current and the effect of dilution due to sample addition.
Figure 11:
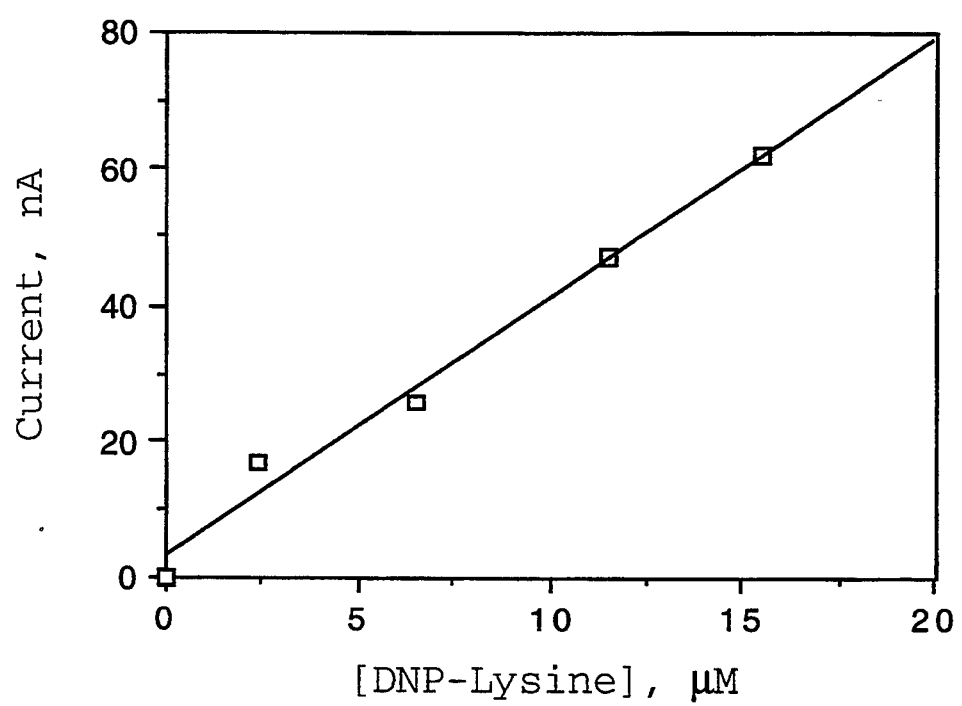
FIG. 11 shows a plot of catalytic current with a three electrode microcell. The sample was 50% urine, with $H_2O_2$ added to 10 mM, antibody at 2.0 mM, Mediator-ε-2,4-DNP-L-lysine conjugate at 1.25 mM. The background electrolyte is 0.05M potassium phosphate buffer, pH 7.0. Corrections were made to eliminate background current and the effect of dilution due to sample addition.

A series of ε-2,4-DNP-L-lysine concentrations was tested with an immunosensor prepared as described in Example 3. The immunosensor responded with increasing catalytic current to concentrations of ε-2,4-DNP-L-lysine antigent in water and urine samples ranging from 0 mM to over 25 mM as shown in FIGS. 10 and 11 respectively.

Measurement of ε-2,4-DNP-L-Lysine

Electrochemical detection of the enzyme amplified antibody reaction in a homogeneous competitive immunoassay was quantitatively determined using the HRP electrode coupled to the ε-2,4-DNP-L-lysine/anti-DNP antibody immuno reaction. Incremental amounts of ε-2,4-DNP-L-lysine were added to the immunosensor and the current recorded after each addition. The immunosensor responded with increasing catalytic current to concentrations of ε-2,4-DNP-L-lysine antigen ranging from 0 to over 2.0 μM. The linear response was from 0 to 1.0 μM (see FIG. 10). The limit of reliable detection is dictated by the dissociation of the antibody antigen pair. The dissociation constant is 0.05 μM. The lower detection limit was thus determined by the binding of the antibody antigen pair and not by the immunosensor design.

ε-2.4-DNP-Lysine in Blood and Urine

Two samples were tested: whole blood and urine. Whole blood was found to inhibit the HRP enzyme electrode. This inhibition was completely reversed when whole blood was removed and the electrode washed. Urine also reduced the catalytic current and gave a larger background current but the HRP electrode was still operating effectively. Addition of a surfactant, e.g., 0.5% Tween 80 or alternatively, Triton X-100, Tween 20, etc., improved sensor response due to minimization of background current. FIG. 11 shows a plot of the catalytic current vs. known concentrations of ε-2,4-DNP-L-lysine added to the urine sample. The stability of the three electrode cell immunosensor in the presence of biological samples like urine is evidence of stability when screening human exposure to toxic substances.

Interferences can inhibit sensor response to the presence of analyte or cause a background current unrelated to analyte concentration. Background current for this electro-immunosensor in the samples tested and the experimental results shown in FIGS. 10 and 11 have been corrected for this contribution.

EXAMPLE 4

This example provides a description of two electro-immunosensors which were designed to indicate analyte levels by an increase in the electrical current. The devices incorporating these electro-immunosensors were less sensitive than the electro-immunosensor of Example 5. The two electrodes utilize different methods of antibody incorporation.

In the first system, an anti-atrazine antibody was mixed in an electrochemical cell with an atrazine-ferrocene complex in an electrochemical cell equipped with a horseradish peroxidase electrode. In the second system, the anti-atrazine antibody was first immobilized on colloidal gold, then deposited onto the electrode surface. An atrazine-horseradish peroxidase conjugate was then added to the electrochemical cell. Both systems were then tested to determine what happened to the amperometric current when analyte, i.e., atrazine was added to the cell.

Antibodies Specific for Atrazine

Polyclonal antibodies raised in rabbits against atrazine were obtained from Biodesign, Inc. (Kennebunkport, Me.). All antibody stock solutions were dialyzed against three changes of 2 mM phosphate buffer pH 8 for 24 hours. The antibody was kept at this low molarity buffer for as short a time as possible. The dialyzed antibody was centrifuged at 14,000 rpm for 20 minutes at 4° C. to remove any microaggregates.

In experiments utilizing a ferrocene-atrazine complex, anti-atrazine antibody was added to the sample solution of the working cell shown in FIG. 1. For each milliliter of sample solution, 3 μl serum (10–30 mg/ml of globulins) was added. This antibody, free in solution, bound the atrazine-ferrocene conjugate and eliminated the catalytic current of the HRP enzyme electrode.

Figure 5:
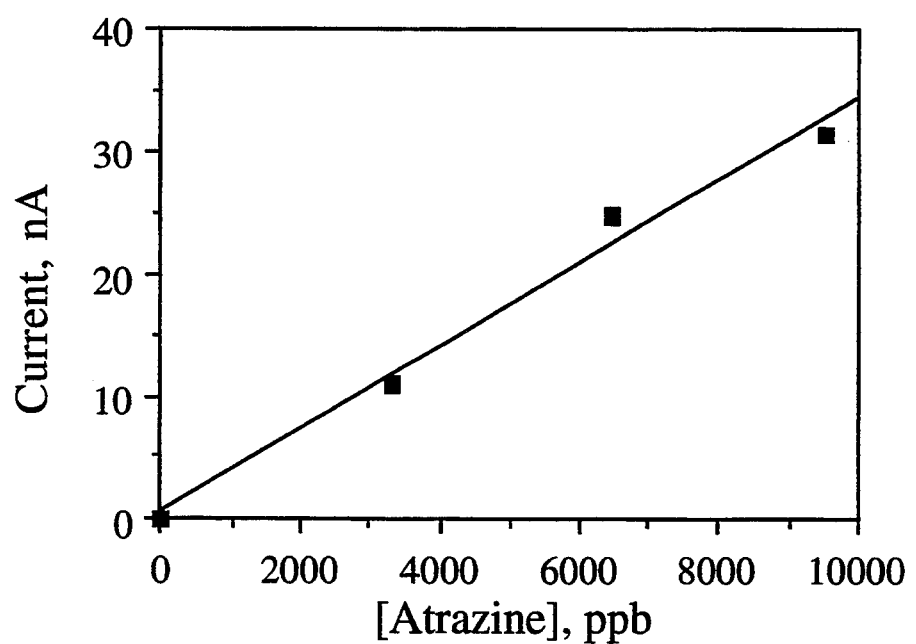
FIG. 5 is a plot of catalytic current obtained with atrazine in the presence of 20 μM ferrocene-atrazine conjugate. The background electrolyte is 50 mM phosphate, pH 7.0, 10 mM in NaCl. The substrate was fixed at 0.5 mM $H_2O_2$.

As shown previously, increasing ferrocene-atrazine concentration led to increasing catalytic current (FIG. 4) while addition of anti-atrazine antibody to the solution eliminated the current. Known amounts of atrazine were added to the sample solutions for electro immunochemical detection in order to establish a response range for the analyte. The theoretical limit of detection with this system is expected to be about 10 ppb. Nonoptimized results shown in FIG. 5 were two orders of magnitude above the theoretical limit.

EXAMPLE 5

ONE STEP ELECTRO-IMMUNOSENSOR DETERMINATION OF ANALYTE

An important objective in the design of an electro-immunosensor system is to obtain a proportional response to atrazine concentration in a one-step process.

As shown in Example 3, the response limit of the ferrocene atrazine mediator was about 10 ppb. Therefore, the inventors prepared a novel electro-immunosensor design that does not depend on low mediator concentrations. As described in the following example, an anti-atrazine antibody was first immobilized on colloidal gold. HRP-atrazine conjugate was then added to the electrode surface and allowed to bind to the immobilized antibody. Performance of this electro-immunosensor was at least 1 order of magnitude greater than the electro-immunosensor designs described in Example 4.

Figure 6:
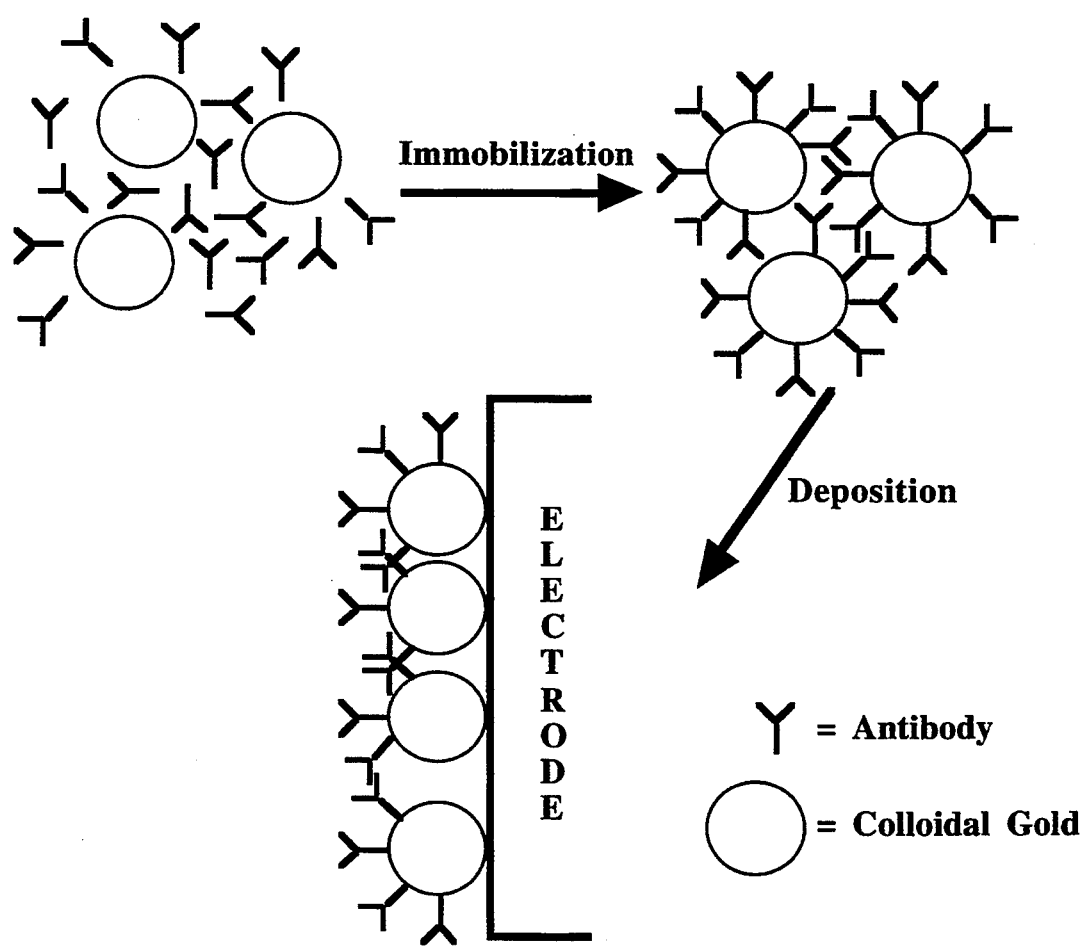
FIG. 6 is an illustration of antibody immobilization on colloidal gold and deposition on a carbon electrode.

The deposition of the colloidal gold adsorbed anti-atrazine antibody is illustrated generally in FIG. 6. An antibody colloidal gold solution was prepared by first determining the minimum amount of antibody required for stabilization of the colloidal gold. This was done using a variation of the method of Horisberg, et al., 1975 as follows: A serial dilution of the antibody in water was prepared, and 10 $\mu$l of each dilution was added to 50 $\mu$l of colloidal gold and rapidly mixed. After 1 minute, 10 $\mu$l of a 10% NaCl solution was added, mixed rapidly, and allowed to stand for 5 minutes. Unstable solutions turned from red to blue. The minimum amount of antibody required to maintain the red color of the colloidal gold solution determined the ratio employed for immobilizing the anti-atrazine antibody to the gold. To form the electrode, 3 $\mu$l of the antibody gold solution was evaporated onto a glassy carbon electrode.

The presence of active antibody on the electrode surface was confirmed electrochemically. After drying the antibody-gold film, the electrode was incubated with a solution of HRP-atrazine conjugate for 15 minutes. The electrode was then washed 3 times with water. A standard HRP electrode sample solution (50 mM phosphate pH 7.0, 10 mM NaCl, 0.5 mM $H_2O_2$, 20 nM ferrocene) was placed on top of the electrode and a catalytic current was observed.

Figure 8:
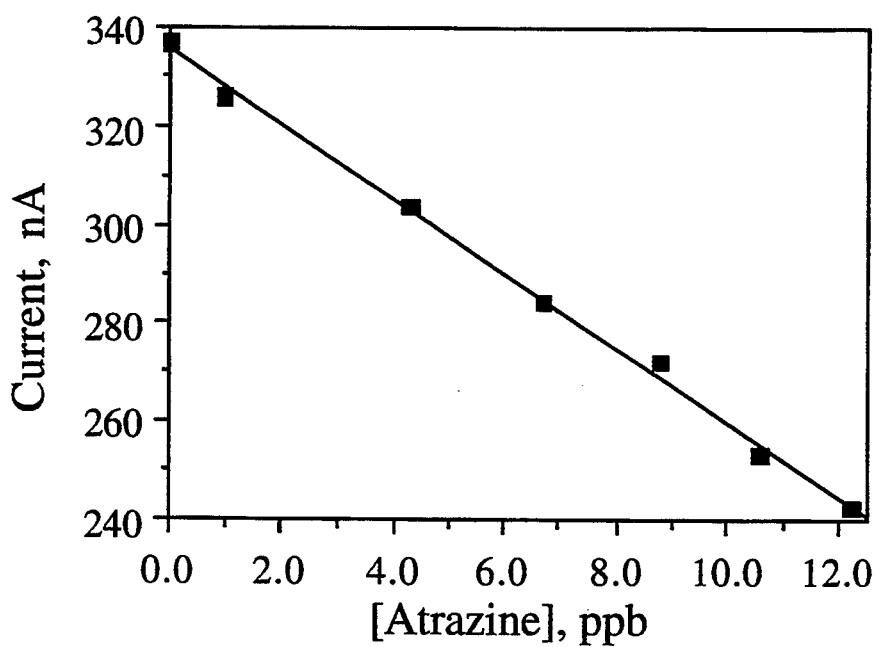
FIG. 8 is a plot of catalytic current obtained with atrazine in the presence of 20 μM ferrocene. The background electrolyte is 50 mM phosphate, pH 7.0, with 10 mM NaCl. Substrate concentration is fixed at 0.5 mM $H_2O_2$.

To use this electro-immunosensor to determine analyte concentrations, 50 $\mu$l of anti-atrazine polyclonal serum diluted 1/100 to colloidal gold was adsorbed to the colloidal gold, deposited onto the surface of a glassy carbon electrode, followed by incubation with an atrazine-HRP complex. Addition of atrazine to the electrochemical cell caused a decrease in amperometric current proportional to the amount of atrazine added. This enabled detection of atrazine at 1 ppb. A standard curve, shown in FIG. 8, was determined employing samples with 0.02–0.12 mM atrazine.

Apparatus for Electro-Immunosensor Detection of Atrazine

Figure 7:
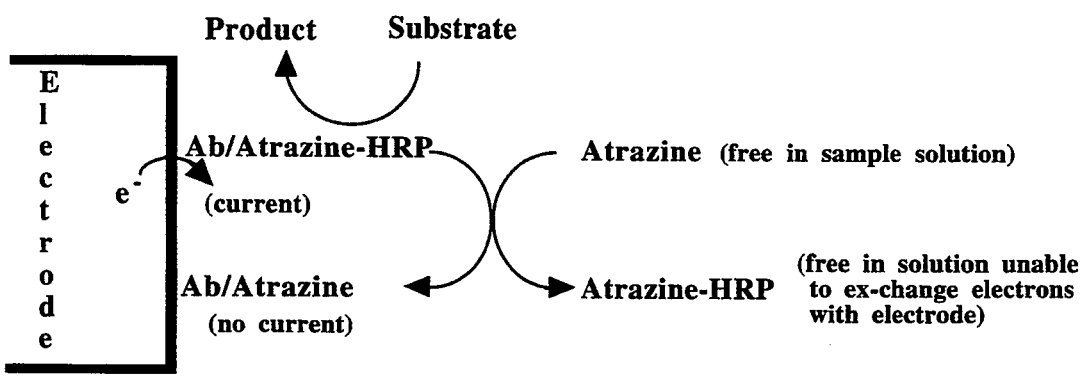
FIG. 7 is a schematic representation of an electro-immunosensor which detects Atrazine, or other analytes at concentrations as low as 1 part per billion. Antibody binds the atrazine-HRP conjugate, localizing HRP at the electrode surface thereby allowing electron transfer. This results in a catalytic current in the presence of $H_2O_2$. Added analyte displaces the analyte-HRP complex from the antibody, effectively removing HRP from the electrode surface. Electron transfer is inhibited so that loss of catalytic current is proportional to the amount of analyte in the sample.

The particular electro-immunosensor design shown in FIG. 7 employs a horseradish peroxidase electrode to provide "amplification" for the detection of displacement of HRP antigen conjugate from the antibody by the analyte. As described herein, the analyte is the compound one wishes to detect. Amplification occurs because the displacement of the HRP antigen-conjugate by free analyte results in a loss of HRP function and hence, a decrease in the flow of electrons from the electrode to the enzyme via electron transfer. This decrease in the flow of electrons, i.e., catalytic current, indicates the presence of the analyte in the test solution.

In contrast to the devices described in Example 4, the design of the system shown in FIG. 7 provides maximum catalytic current when atrazine is at zero concentration. The current decreases with increasing atrazine concentrations and provides greater sensitivity. An advantage of this system is that a very low level of an electron transfer mediator is not required, and in fact the best response is achieved at saturating levels of mediator. This simplifies measurement because mediator is not a variable component of the current response.

In this novel immuno electrosensor design, the apparent concentration of the anti-atrazine antibody determines the limit of detection. Since the current response is directly proportional to the number of atrazine-HRP conjugates bound to the electrode, and the number of bound conjugates is in turn proportional to the number of active antibody sites immobilized on the electrode surface, care must be taken to insure that an acceptably low number of atrazine-HRP conjugates are bound. For example, for a low concentration of atrazine (e.g., 1 ppb) to be measurable, the total number of atrazine-HRP conjugates bound must not be too large relative to 1 ppb.

EXAMPLE 6

BIOSTRIP ELECTRO-IMMUNOSENSORS FOR ANALYTE DETECTION

Having established a sensitive electro immunobiosensor system, several practical forms of the same invention were contemplated as biosensors. The example below illustrates one example of a reusable test strip biosensor one might employ to detect atrazine, or for that matter, trace levels of other organic compounds. The particular design can incorporate convenient features required by the target market, such as size, shape or the type of specific material employed as substrate, all of which are well within the skill and knowledge of those skilled in the art.

Disposable Test Strip Electro-Immunosensor for Atrazine

There is a need to simplify the fabrication of strip biosensors such that deposition of an immuno-recognition layer on a base sensor is amenable to mass production. Screen printed electrodes are particularly adaptable to this purpose. Screen printed carbon black electrodes may be purchased from Cranfield Biotechnology, Ltd. (Newport, Isle of Wright, p030 5XB, England) or prepared as described below. The screen printed electrodes were formed in batches on a plastic substrate and sliced into individual sensor electrodes, FIG. 9. The next step was deposition of an anti-atrazine antibody colloidal gold conjugate layer on the carbon working electrode.

Figure 18:
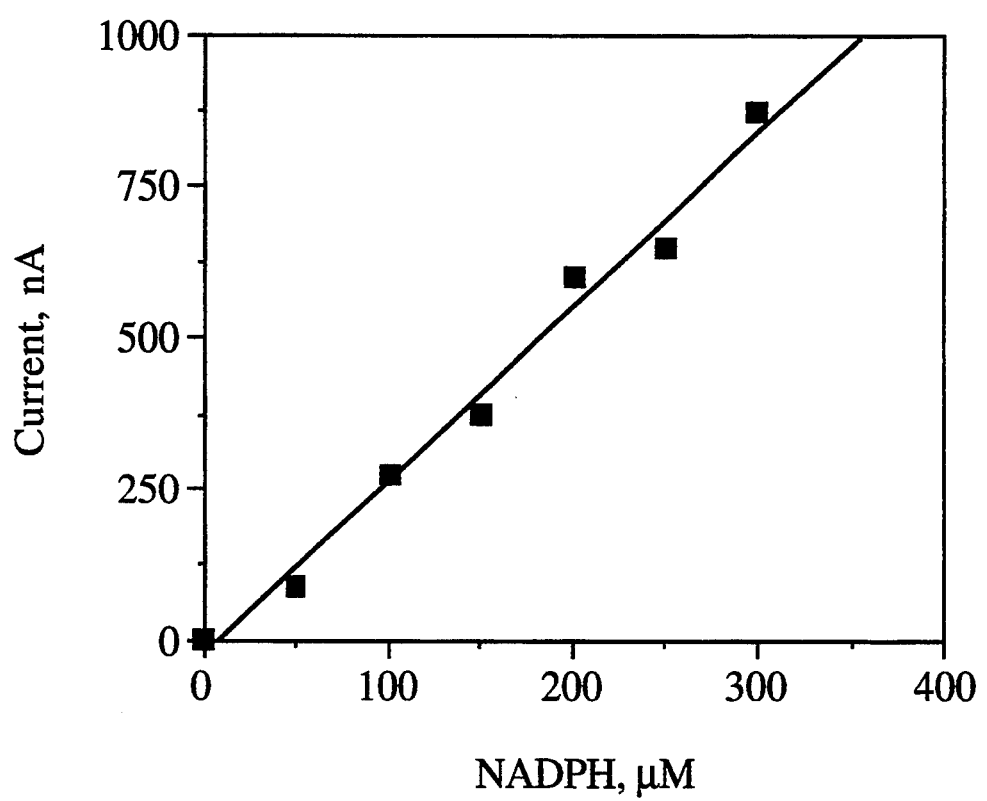
FIG. 18 shows the electrochemical response to NADPH of a test-strip electrode with an electron transfer mediator incorporated in the working electrode.

The electrodes were primed using a polyester screen of 240 mesh and a 36.25° angle. Strips were prepared by thoroughly mixing a mediator with carbon ink (DuPont, Research Triangle Park, N.C.) at room temperature and then primed through the polyester screen onto a 0.5 mm thick plastic substrate. Electrical contact to the electrode as well as the reference and counter electrode were screen printed from silver ink. The strips were tested using redox mediators for AND(P)+-dependent dehydrogenase amperometric biosensors. The phenoxazine modified strip showed potential for the oxidation of enzymatically produced NADPH. The results are shown in FIG. 18. In this design the mediator is incorporated into the test-strip electrode. When samples containing free analyte were added on top and adsorbed by the spreading cover, they contacted the electrode array and displaced the anti-analyte antibody/anti-IgG-HRP conjugate.

Anti-atrazine antibody was immobilized on colloidal gold at the optimal loading by methods described in the previous examples. Anti-atrazine colloidal gold conjugate may also be deposited on the carbon working electrode as previously described. A solution of HRP atrazine conjugate was added to the electrode surface and the conjugate allowed to bind. A mediator solution was added to the electrode surface and dried. This forms a stable, solid state, ready-to-use device.

Five atrazine solutions with concentrations of 0, 0.1, 1, 10, and 100 ppb may be prepared. Test strip atrazine electro-immunosensors can be tested with this standard series. Testing the test strip with field samples will confirm lack of interferences in using this particular type of electrode.

Shelf life and stability of the test strip can be readily determined. Three lots of 5 strips are stored identically at $-10°$, $4°$ and $25°$ C. for one day, one week, one month, three months, six months, nine months, and one year. Each lot is tested after the designated storage time with the standard series of atrazine concentrations (0, 0.1, 1.0, 10, and 100 ppm). An atrazine response profile is then determined.

EXAMPLE 7

DUAL ANALYTE DETECTION IMMUNOSENSOR

A dual-analyte dual-signal immunosensor allowing detection of a separate signal for each analyte has been developed by the inventors. This procedure requires immobilization of two different antibodies on an electrode surface. In this example illustrating the invention, a dual-analyte biosensor electrode was constructed for monitoring two reproductive hormones, follicle stimulating hormone (FSH) and luteinizing hormone (LH). FSH response was linked to the reducing enzyme horseradish peroxidase (HRP) and the LH response was linked to glucose oxidase (GOD).

Anti-FSH antibody conjugated to HRP was obtained from Medix Biotech Inc. (Foster City, Calif.). The enzyme-conjugate reagent contained monoclonal anti-FSH antibody specific for the alpha subunit of the hormone. Monoclonal anti-human FSH antibody was purchased from OEM Concepts, Inc. (Toms River, N.J.). The unconjugated antibody was specific for the beta subunit of the hormone. Anti-LH antibody conjugated to GOD and monoclonal anti-human LH antibody were obtained from Medix Biotech, Inc. The enzyme-conjugate reagent contained monoclonal anti-LH antibody specific for the alpha subunit of the hormone. The unconjugated antibody was a monoclonal anti-FSH antibody specific to the beta subunit of the hormone.

Preparation of Dual Analyte Biosensor

Colloidal gold solutions were prepared as previously described to provide gold particles having a diameter of approximately 300Å. Anti-FSH or anti-LH was immobilized on colloidal gold by first immobilizing protein A from *Staphylococcus aureus* (Sigma Chemical Company, St. Louis, Mo.) on colloidal gold followed by binding the antibodies to the colloidal gold through the protein A.

The gold solution was first concentrated by centrifugation at room temperature at 9,000 rpm for 45 minutes. The concentrated solution was then added dropwise to a stirred solution of protein A on ice. Protein A was absorbed onto colloidal gold by adding at a ratio of 60–100 mg protein A per gram of gold. Dialysis was not required as the protein A was essentially salt free.

Protein A had several advantages for use as a binding agent including: 1) relatively small size which allowed virtually complete coating of the colloidal gold surface thereby significantly reducing background current due to catalytic reaction between hydrogen peroxide and gold surface; 2) binding of antibodies through the $F_c$ region so that there was no interference with antibody-antigen binding; 3) the well-understood nature and structure of the binding between protein A and the antibodies, and 4) the high affinity of protein A to antibodies.

Protein A colloidal gold sol was deposited on a glassy carbon electrode surface and allowed to dry. The electrode surface was then washed with distilled water to remove unbound protein A and coated with 10 µl of a solution containing monoclonal anti-fi FSH or anti-$\beta$ LH in phosphate buffered saline (PBS), pH 7.4. PBS is prepared by mixing 8.0 g of NaCl, 0.2 g of $KH_2PO_4$, 2.9 g of $NA_2HPO_4 \cdot 12H_2O$, 0.2 g of KCL. The solution may be stored at $4°$ C. The freshly prepared electrodes were then incubated at $37°$ C. for 30 minutes.

Spectrophotometric Measurement of FSH and LH

The dual analyte immunosensors were tested spectrophotometrically using a microtiter plate reader. It was first established that the selected HRP-labeled antibody and the capture antibody did not interfere with each other in the binding of FSH or LH. Selected capture antibodies, i.e., anti-$\beta$ subunit FSH and anti-$\beta$ subunit LH were bound to protein A-coated microtiter plate wells. Various concentrations of purified FSH or LH were then added to the wells followed by incubation of HRP-labeled anti-$\alpha$ subunit antibody conjugate. The enzymatic activity of the anti-$\beta$ subunit antibody-immobilized HRP conjugate was determined by spectrophotometric assay with 2,2'-azino-bis(3-ethylbenzthiazoline-6-sulfonic acid) (ABTS) as a secondary substrate in acetate buffer, pH 4.5. The assay mixture contained 2 mM ABTS and 1 mM $H_2O_2$. Absorption was measured at 405 nm.

Figure 12:
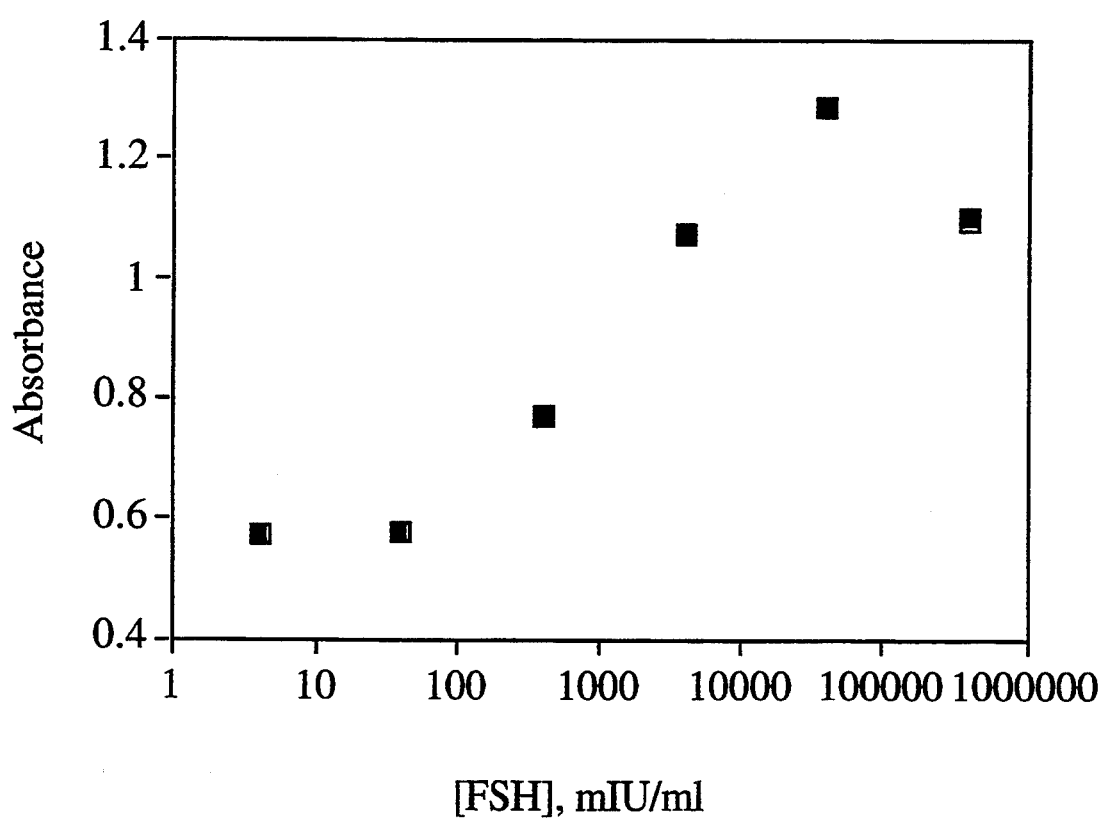
FIG. 12 shows the spectrophotometric response of immobilized anti-β FSH subunit antibody-HRP conjugate measured at 405 nm in a standard ELISA.

The antibody pair chosen for two-site immunoassay detection and measurement of FSH was suitable, as evidenced by the FSH concentration profile shown in FIG. 12. Signal increased in direct proportion to FSH concentrations. FSH response became saturated at approximately 40 IU FSH per ml. Further increases in the FSH concentration resulted in a decrease in signal consistent with the well established prozone effect in immunometric assay. The sensitivity of the spectrophotometric assay was approximately 40 mIU FSH per mL.

Figure 13:
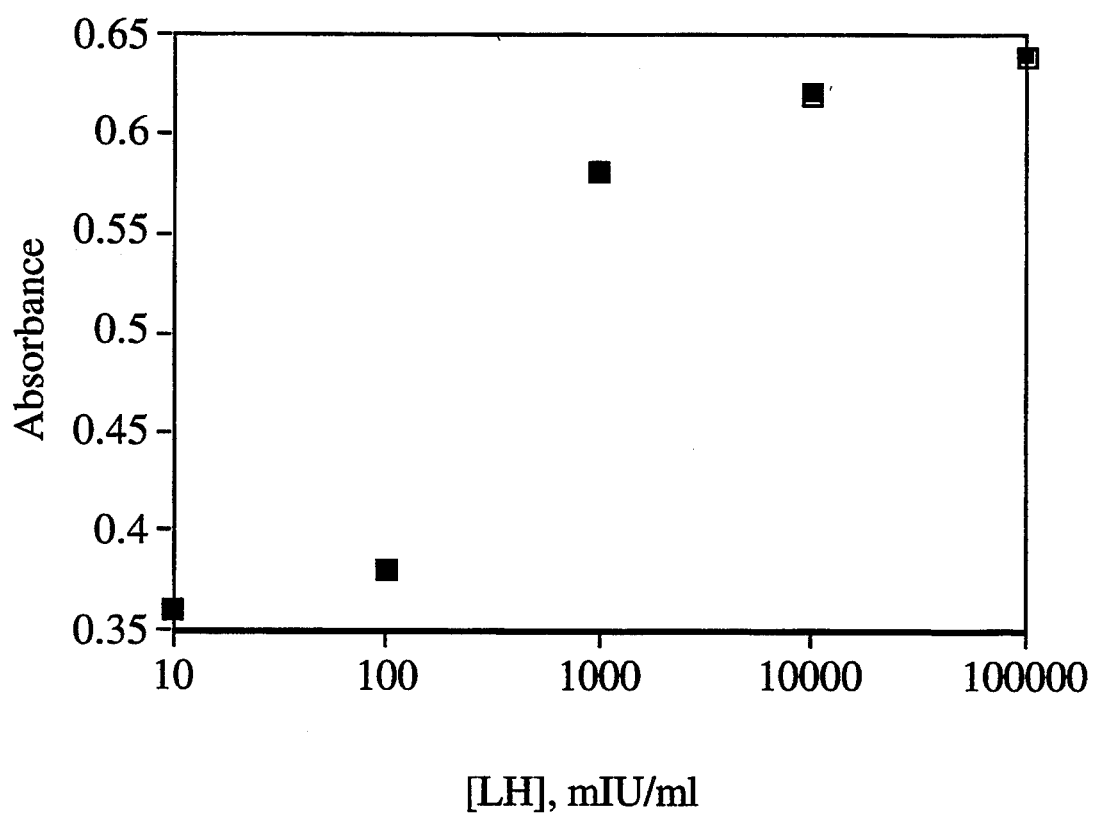
FIG. 13 shows the spectrophotometric response of the immobilized anti-β-LH subunit antibody-HRP conjugate measured at 405 nm in a standard ELISA.

Likewise, the antibody pair chosen for two-site enzyme immunoassay detection to measure LH was suitable, as evidenced by the LH concentration response profile shown in FIG. 13. The results indicated that saturation was approached at approximately 100 IU LH per ml. The sensitivity of the spectrophotometric assay was approximately 10 mIU LH/mL.

Measurement of FSH and LH

The levels of FSH and LH were measured in urine samples using the electro-immunosensor. There are two principal interferences that can disrupt the proper operation of the electro-immunosensor. These include nonspecific inhibition of the catalytic current and nonspecific contributions to the catalytic current. The first interference masks increases in catalytic current regardless of FSH and LH concentrations and contributes to false negative results. The second interference causes an increase of catalytic current unrelated to FSH and LH concentration and contributes to false positive signals. It will be recognized that treated human urine potentially contains agents that can cause either one of this type of interference. The first type of interference may be caused by HRP and GOD inhibitors such as amines and heavy metals, consumers of $H_2O_2$, such as catalase, agents that cross react with anti-FSH or anti-LH antibodies such as other hormones, proteins and metabolic degradation of the target hormones. The second type of interference may be caused by nonspecific absorption of the enzyme-antibody conjugates at the electrode surface and redox active species that will reduce at the electrode at operations potentials. The following example illustrates contemplated assay procedures.

Electro-immunosensors prepared as described were used to measure FSH and LH in aqueous samples. The samples were placed in contact with the immunosensors and incubated at 37° for 30 minutes, and soaked in monoclonal anti-$\alpha$ subunit FSH conjugated to HRP or anti-$\alpha$ subunit LH conjugated to HRP at 37° for 30 minutes. This resulted in a sandwich of FSH or LH molecules between the electrode and enzyme-linked antibodies. Because of the different specificities, one antibody attached to the electrode and the other conjugated to HRP did not compete for binding to FSH or LH. This made it possible to complete the two antigen-antibody reactions in a single short incubation.

The electrochemical response of FSH and LH two-site immunoassay electrodes was measured in 50 mM phosphate buffer, pH 6.8 containing 10 mM KCL. The assay solution consisted of ferrocene carboxylic acid (electron transfer mediator) and hydrogen peroxide (HRP substrate). Concentration of both substances was fixed at 0.5 mM which is well into the region where the electrode response is independent of the concentrations of these components. Silver wire and platinum were used as reference and counter electrodes respectively. Three electrode microcells were used with either 5 ml or 20 $\mu$l volume. The two-site immunoassay glassy carbon electrodes were constructed as previously described.

Figure 14:
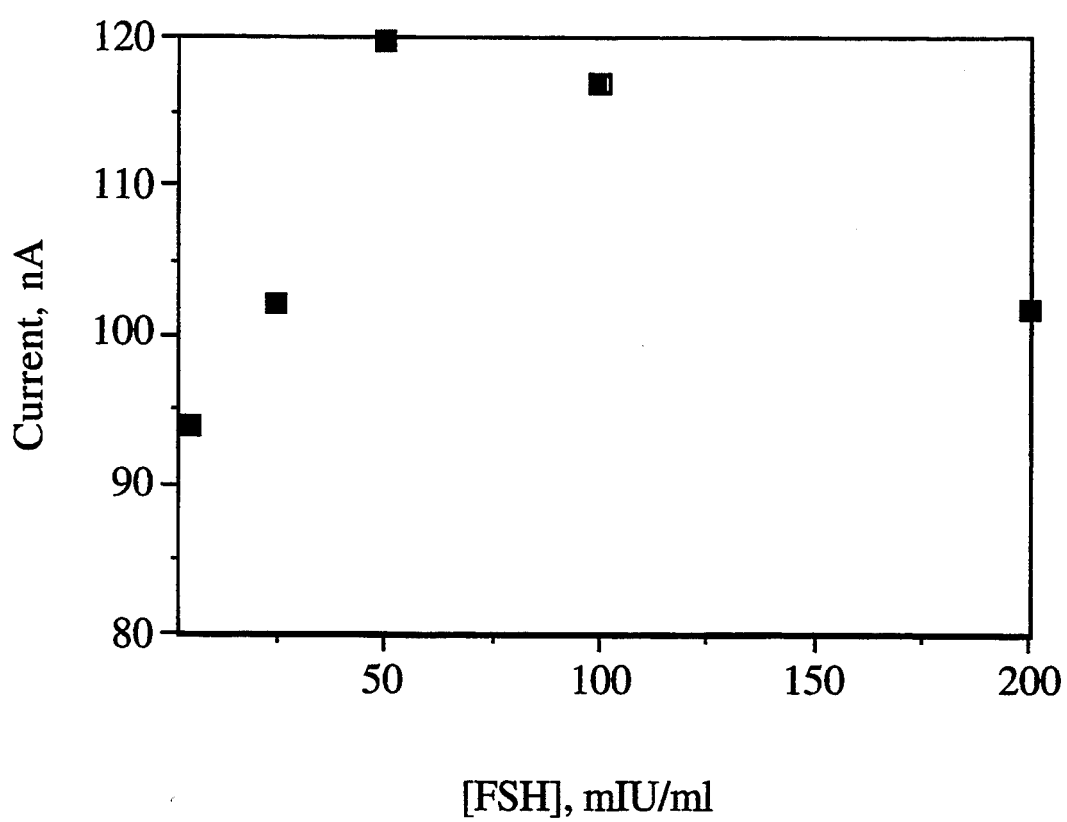
FIG. 14 shows the electrochemical response of immobilized anti-β FSH subunit antibody-HRP conjugate to FSH in aqueous solution.

The electro-immunosensor response to FSH concentrations where catalytic current of HRP enzyme increases with FSH concentrations to around 50 mIU FSH per ml followed by a decrease of the current at FSH concentrations associated with the prozone effect in immunometric assay is shown in FIG. 14. The electrochemical assay was at least two orders of magnitude more sensitive than the spectrophotometric assay, the results of which are shown in FIG. 12.

Figure 15:
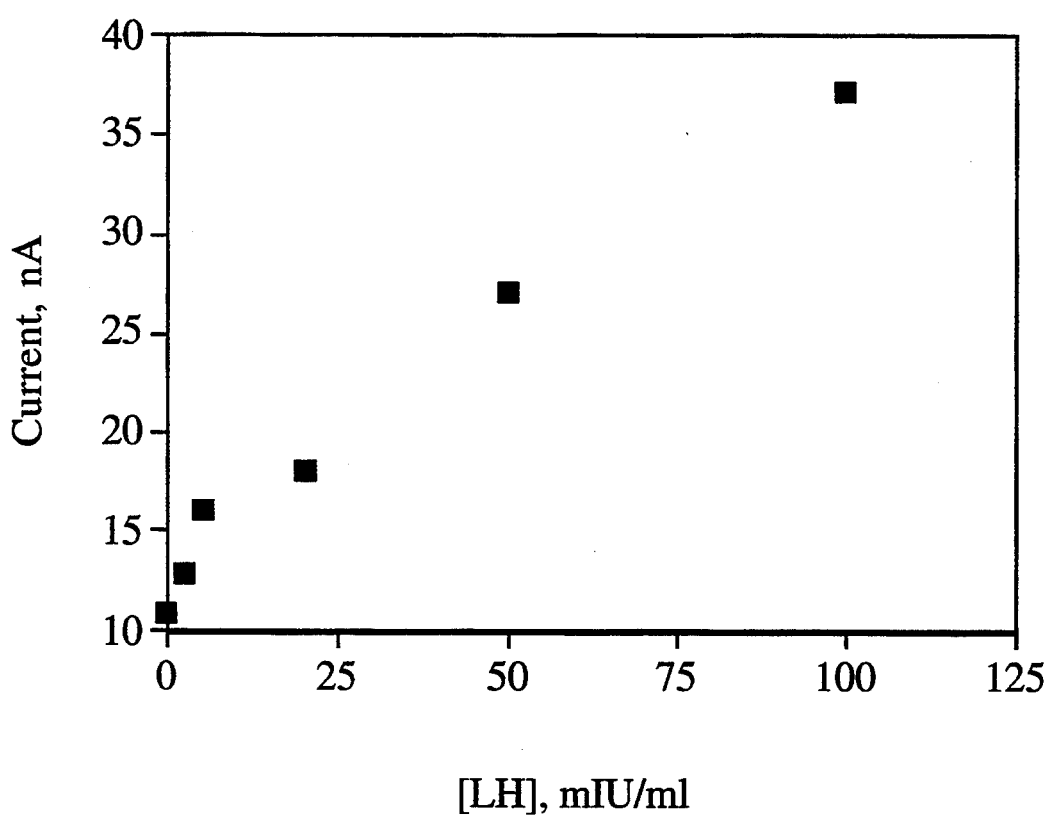
FIG. 15 shows the electrochemical response of immobilized anti-β-LH subunit antibody-HRP conjugate to LH in aqueous solution.

FIG. 15 shows the electro-immunosensor response to LH concentrations where catalytic current of the HRP enzyme increases with LH concentrations to at least 100 mIU LH per ml. Again, the electrochemical assay was more sensitive than the spectrophotometric assay by at least two orders of magnitude (FIG. 13).

EXAMPLE 8

ALTERNATIVE DESIGNS OF THE DUAL IMMUNOSENSOR

The electro-immunosensors described in Example 7 utilize a noncompetitive two-site assay between immobilized antibody, free analyte and enzyme labeled antibody. Several possible immunosensor designs based on the invention provide simultaneous dual analyte detection. Two of these designs are described in this example; one design employs two separate detection electrodes and the other design employs a single detection electrode. In each case, the system provides a dual-analyte redox enzyme electro immunoassay method that is homogeneous and separation-free. The design is amenable to the development of reliable easy to use portable sensors for two related compounds. In the designs illustrated, discussion is directed to detection of FSH and LH; however, this is only to provide a particular model as the designs are of general application.

Design Number 1

In this configuration, there are two recognition reactions occurring in parallel. Each reaction uses different analytes and antibodies but the same enzyme label (HRP). Reactions take place on two separate electrodes, see FIG. 16, in close proximity and are exposed to the same sample. The antibody recognition of each analyte is coupled separately to the system's electrical response so that when a potential is applied the response due to each analyte is resolved and each concentration value is measured independently.

The dual detection electrode test strip immunosensor's operational design involves two biochemical systems. The first system specifically recognizes the target analyte with the monoclonal antibody specific for the beta subunit and then localizes the redox enzyme label at the electrode surface with a monoclonal antibody specific for the alpha subunit. The second system converts the antibody detection into electron flow and amplifies the detection by generating numerous electrons for each antibody bound analyte.

Figure 16:
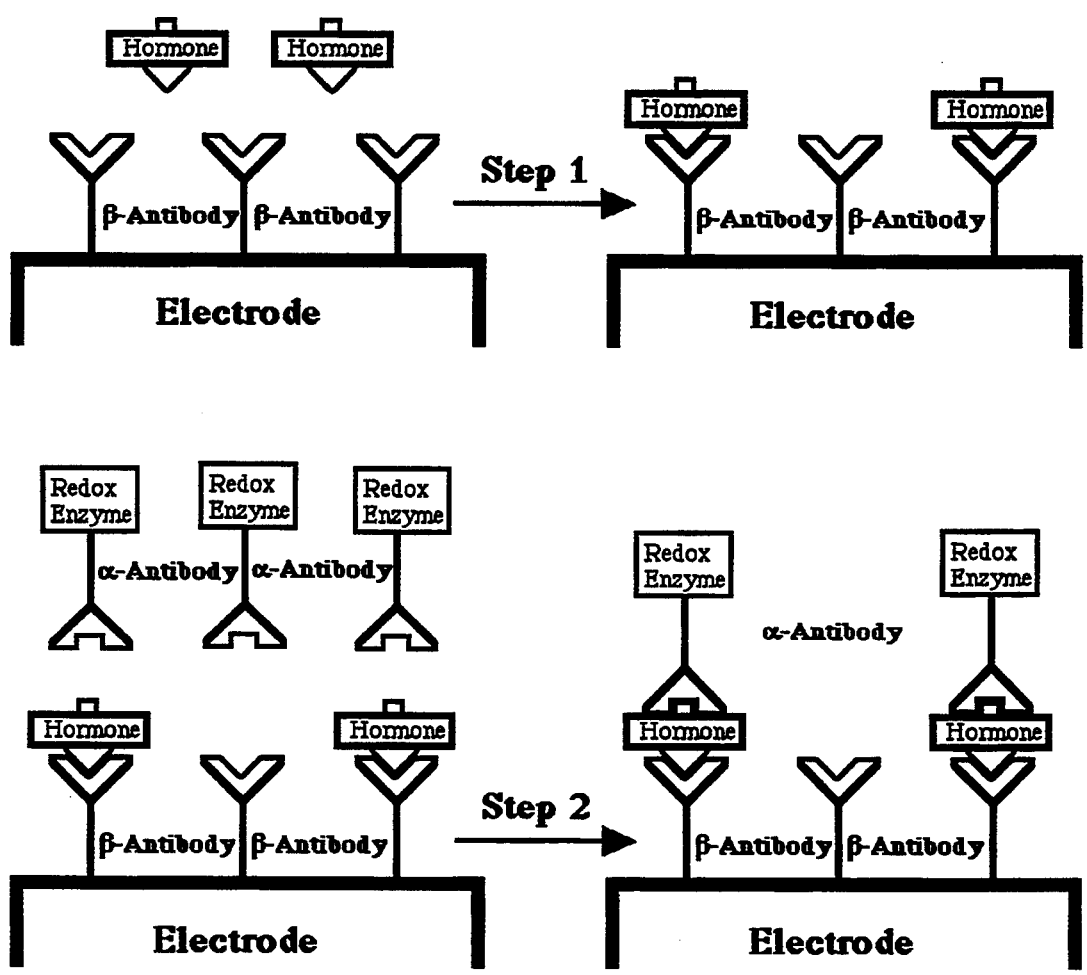
FIG. 16 is a schematic representation of a recognition/localization system on one channel of a dual detection electrode immunosensor.

In the recognition localization system shown in FIG. 16, the anti-$\beta$ subunit antibody is immobilized on the specific electrode of the test strip electro-immunosensor via colloidal gold using procedures described. When the test strip is exposed to a sample containing a hormone to which the anti-$\beta$ subunit antibody specifically binds, an amount of the hormone proportional to the concentration in the sample will bind at the electrode surface. This constitutes the recognition step or step 1. The anti-$\alpha$ subunit antibody redox enzyme conjugate that is present in the test strip then binds to the hormone attached to the electrode surface. This constitutes the localization step or step 2. The enzyme located at the electrode surface is detected and measured electrochemically. It has been shown that the redox enzyme free in solution does not contribute significantly to the signal. This permits one to conduct the electro immunoassay without need for separation.

Design Number 2

Figure 17:
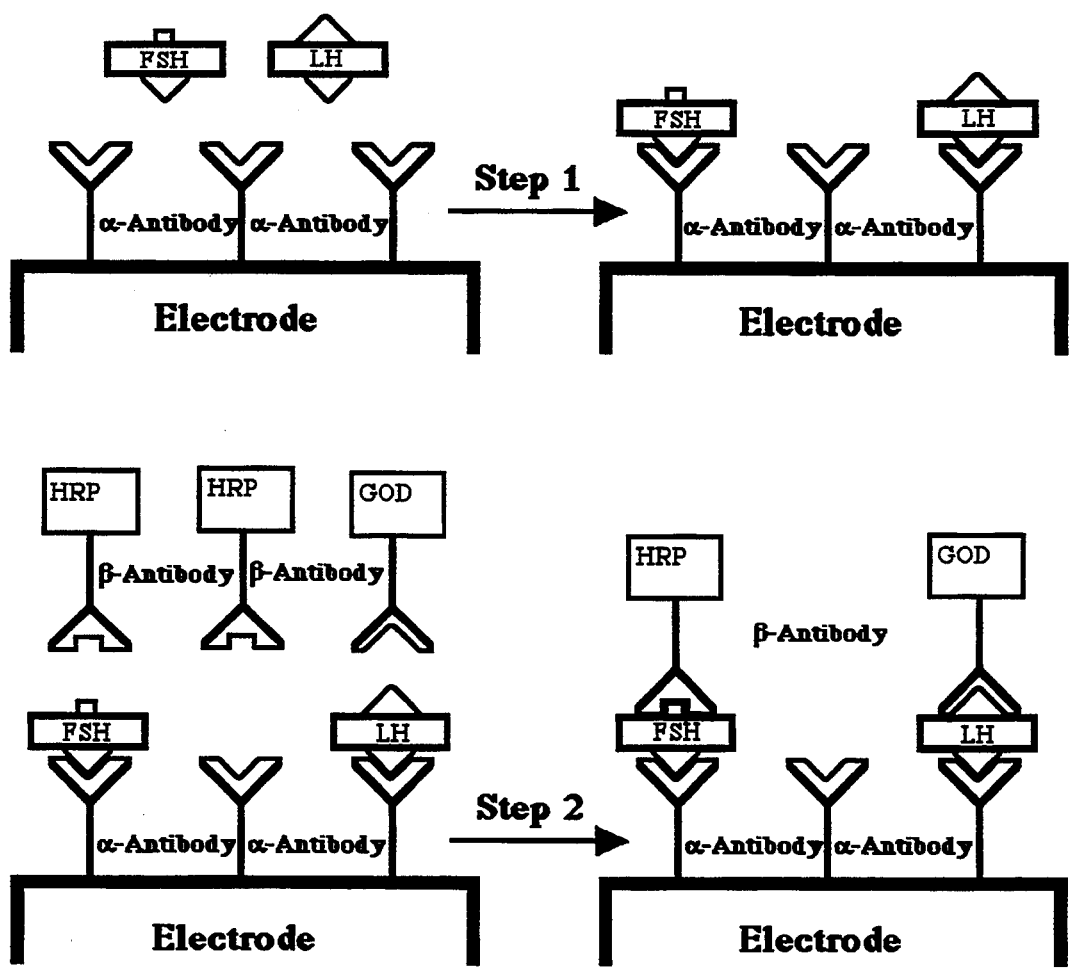
FIG. 17 is a schematic representation of a dual analysis recognition/localization system on a dual detection electrode immunosensor.

An alternative design utilizes two recognition reactions occurring in parallel with different analytes, enzymes and antibodies but taking place on a single electrode, see FIG. 17. The antibody recognition of each analyte is coupled separately to the system's electrical response by the different oxido-reductase nature of the two enzymes, contemplated to be HRP and glucose oxidase (GOD) so that when potential is applied the response due to each analyte is resolved and each concentration value measured independently.

Single-detection electrode strip immunosensor operational design consists of two biochemical systems. The first system captures both FSH and LH with a monoclonal antibody specific to the $\alpha$-subunit and localizes the HRP enzyme label at the captured FSH site and GOD enzyme label at the captured LH sites. The second enzyme converts the antibody detection into electron flow and amplifies the detection by generating many electrons for each antibody bound analyte.

In the recognition localization system shown in FIG. 17, the anti-α subunit antibody is immobilized on a single detection electrode of the test strip electro-immunosensor via colloidal gold using procedures previously described. When the test strip is exposed to a sample containing FSH and LH hormones, the anti-α subunit antibody binds an amount of each hormone proportional in concentration in the sample at the electrode surface. This constitutes the localization step 1. The anti-β subunit FSH antibody-HRP conjugate present in the test strip binds to the FSH attached to the electrode surface and the anti-β subunit LH antibody-GOD conjugate present in the test strip binds to LH attached to the electrode surface. This constitutes the recognition step 2. The HRP localized at the electrode surface is detected and measured electrochemically when a fixed reduction potential is applied. The GOD localized at the electrode surface is detected and measured electrochemically when a fixed oxidation potential is applied.

The alpha subunit of FSH is reported to be identical to the alpha subunit of LH (Shome and Parlow, 1974). The two-working electrode design must have the number of anti-α subunit antibodies conjugated to HRP in excess of the total number of anti-β subunit antibodies immobilized on both working electrodes. The single working electrode design must not use anti-α subunit antibody of the conjugate to the oxido-reductase enzymes because this conjugate would not differentiate FSH and LH. The single working electrode design will have anti-α subunit antibody immobilized on the electrode and anti-β subunit FSH antibody conjugated to HRP and anti-beta subunit LH antibody conjugated to GOD.

The transduction amplification systems for electro-immunosensors linked to HRP and GOD are shown schematically in FIGS. 16 and 17. These systems produce catalytic current within the electro-immunosensor. Amplification occurs after antibody recognition localization because the redox enzyme is sufficiently close to the electrode surface to exchange electrons. The exchange of electrons with the electrode fuels a catalytic turnover of the enzyme substrates present in the electro-immunosensor. Thus for each hormone detected, one redox enzyme is localized at the electrode surface and transfers many electrons to the electrode surface.

EXAMPLE 9

DETECTION OF DRUG METABOLITES

The enzyme immunosensor assays described and illustrated in the previous examples are applicable to a wide variety of analytes. However, certain modifications in design may be required to optimize results or to achieve meaningful measurements. This example illustrates a modification of the anti-analyte immobilization that allowed detection of one of the major metabolites of cocaine, i.e., benzoylecgonine. The same technique is also expected to be applicable to 11-nor-Δ9-tetrahydrocannabinol-9-carboxylic acid, a metabolite of tetrahydrocannabinol.

Benzoylecgonine was immobilized in two separate steps: 1) immobilization of protein-coated colloidal gold onto glassy carbon electrode and 2) covalent binding of benzoylecgonine to the protein on the colloidal gold surface. Colloidal gold sol was surface-coated by adding bovine serum albumin at a ratio of 60-100 mg BSA/g Au. The BSA/Au sol was evaporated onto glassy carbon electrodes. The films were dried, then rinsed extensively to remove excess BSA. Benzoylecgonine was then covalently anchored to colloidal gold through formation of amide bonds between the carboxylic groups on benzoylecgonine and the amine groups on BSA. The covalent binding was accomplished with a modified published procedure in which the formation of amide bonds is generated by the combined action of 1-ethyl-3-(3-dimethylaminopropyl)-carbodiimide (EDC) and N-hydroxy-succinimide (NHS) (Søndergard-Andersen et al., 1990). The covalent binding orients the immobilized analyte in a defined way so that it is easily accessible to antibody.

Deposition of Colloidal Gold on Electrode Surface

Figure 9:
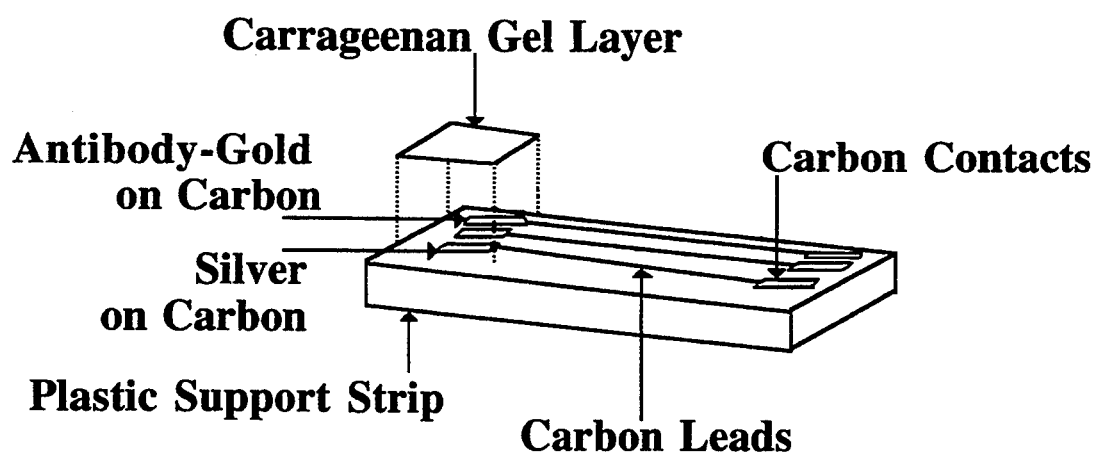
FIG. 9 shows a diagram of a test strip electro-immunosensor configuration consisting of a three electrode microfabricated electrode strip with a carrageenan gel layer incorporating mediator, enzyme-antigen conjugate and other desired reagents.

Colloidal gold was deposited on the electrode surface by evaporation of 3 μl of sol onto the glassy carbon working electrode of a micro-cell (FIG. 9). The films were dried then washed with distilled water. Finally, the electrode was washed with PBS-Tween 20 solution (15 mM phosphate, 0.15M NaCl, 0.5% Tween).

Synthesis of Enzyme-Antibody Conjugates

Goat anti-mouse IgG antibody conjugated to HRP was purchased from PIERCE (Pierce Chemical Company, Rockford, Ill.). The enzyme conjugate reagent contained anti-Mouse IgG antibody specific to the Fc region of monoclonal anti-benzoylecgonine antibody.

Incorporation of Antibody

Monoclonal anti-benzoylecgonine antibody was purchased from Biodesign. This antibody was added in solution to the colloidal gold electrode with immobilized benzoylecgonine. The antibody was incubated with the immobilized analyte to allow binding to the analyte. Unbound monoclonal anti-benzoylecgonine antibody was removed by washing.

Anti-Mouse IgG antibody conjugated to HRP was added in solution to the colloidal gold electrode with immobilized benzoylecgonine/monoclonal anti-benzoylecgonine antibody. The conjugate was incubated with the bound monoclonal antibody and allowed to bind to the analyte. Unbound monoclonal anti-Mouse IgG conjugated to HRP was removed by washing.

Characterization of Electro-Immunosensor

Benzoylecgonine was purchased from Sigma Chemical Company (St. Louis, Mo.).

The antibody and enzyme-antibody conjugate were tested in a benzoylecgonine immunoassay spectrophotometrically by microtiter plate reader. It was determined that the selected monoclonal anti-benzoylecgonine antibody bound to the micro-liter plate immobilized benzoylecgonine and that HRP-labeled anti-IgG antibody bound to the immobilized monoclonal anti-benzoylecgonine antibody.

The enzymatic activity of the plate-bound anti-IgG antibody-HRP conjugate was determined in a spectrophotometric assay with 2,2'-azino-bis(3-ethylbenzthiazoline-6-sulfonic acid) (ABTS) as a secondary substrate in acetate buffer at pH 4.5. The assay mixture contained 2 mM ABTS and 1 mM $H_2O_2$. Absorption was measured a 405 nm.

Figure 19:
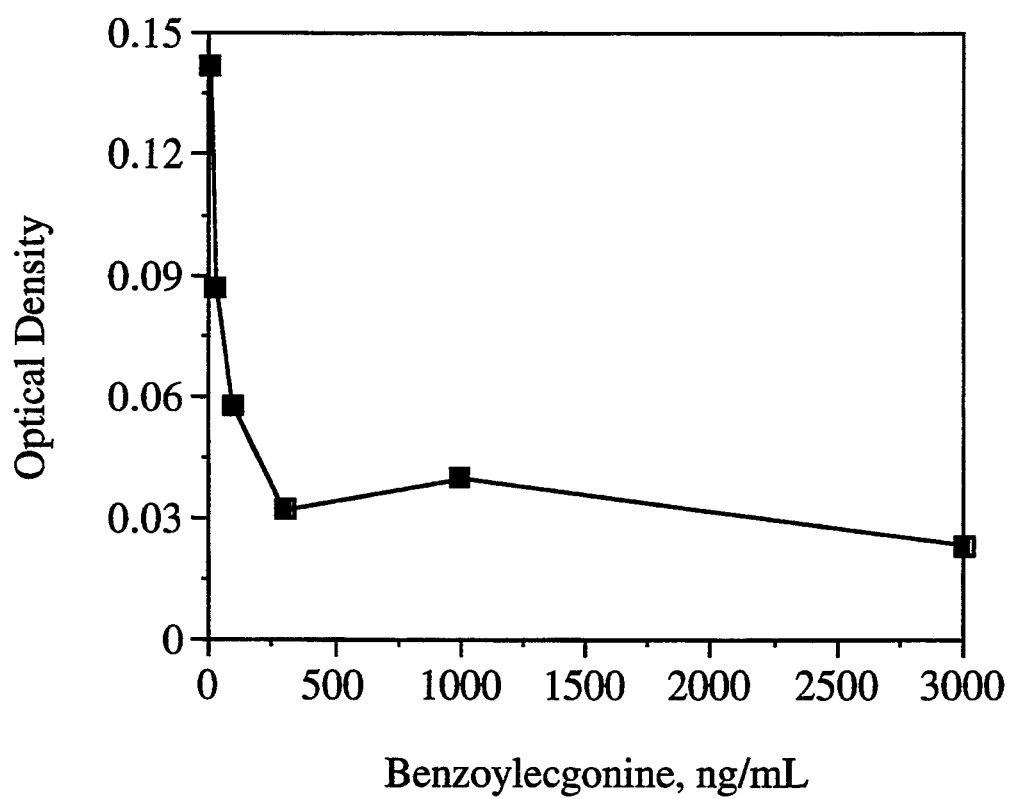
FIG. 19 shows the spectrophometrically determined immunochemical response of benzoylecgonine in a human urine sample. Corrections were made to eliminate background absorbance.

Benzoylecgonine was determined in a urine sample (FIG. 19). This analysis gave a decreasing signal with increasing benzoylecgonine concentrations in human urine. Benzoylecgonine response saturated around 300 ng/mL. The sensitivity of the spectrophotometric assay was ca 30 ng/mL.

The following parameters were varied in order to optimize the microtiter plate assay: (a) the amount of NHS+EDC and the type of coupling buffer in the coupling step; (b) the duration of coupling time; (c) the concentration of the primary and secondary antibody during incubation; and (d) the duration for competition of free benzoylecgonine with electro-immobilized benzoylecgonine. It was observed that the competition of free benzoylecgonine with immobilized analyte was most efficient in a duration of 2–5 minutes.

Detection of Benzoylecgonine and THC Metabolites

Benzoylecgonine was determined electro immunochemically in aqueous samples. Incubation was at room temperature for 5 minutes. Due to the shared specificities, the sample benzoylecgonine competed with the electrode immobilized benzoylecgonine for binding to anti-benzoylecgonine antibody conjugated (via anti-IgG) to HRP. This competition resulted in the displacement of some portion of the anti-benzoylecgonine antibody conjugated to HRP. Displaced anti-benzoylecgonine antibody conjugated to HRP did not undergo electron transfer with the electrode. The amount of anti-benzoylecgonine antibody conjugated to HRP displacement was proportional to the concentration of free benzoylecgonine in the sample.

The electrochemical response of benzoylecgonine competitive immunoassay electrodes was measured in 50 mM phosphate buffer solution at pH 6.8 with 10 mM KCl. The assay solution consisted of ferrocenecarboxylic acid (an electron transfer mediator) and hydrogen peroxide (HRP substrate). Both concentrations were fixed at 0.5 mM which is well into the region where the electrode response is independent of the concentrations of these agents. Silver wire and platinum were used as reference and counter electrodes respectively. Three electrode micro-cells were used with either 5 mL or 20 μl volume.

Figure 20:
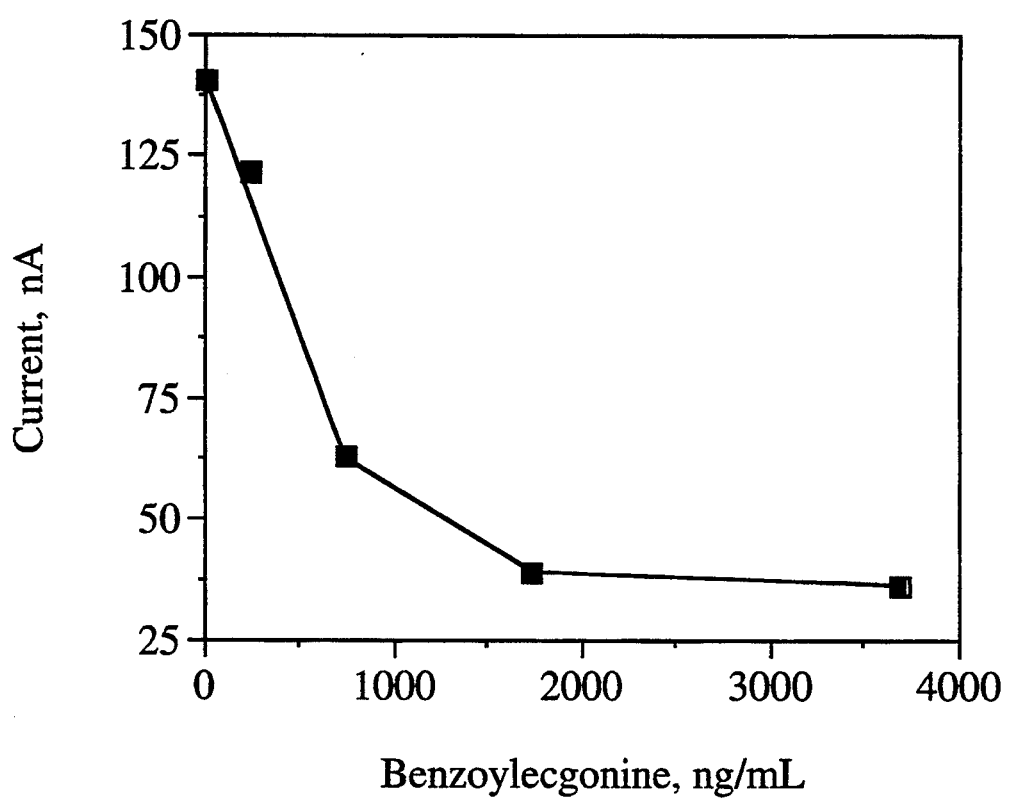
FIG. 20 shows the electroimmunochemical response of benzoylecgonine in aqueous solution.

FIG. 20 shows the electro-immunosensor response to benzoylecgonine concentrations where catalytic current of the HRP enzyme decreases with increasing benzoylecgonine concentrations to around 2,000 ng benzoylecgonine/mL. The electrochemical assay proved to be more sensitive than a spectrophotometric assay (FIG. 14). The sensitivity of electrochemical assay is ca 30 ng benzoylecgonine/mL.

The electrochemical response of benzoylecgonine competitive immunoassay electrodes were then measured in samples 25% 50 mM phosphate buffer solution at pH 6.8 with 10 mM KCl and 75% human urine. The electro-immunosensors were incubated in the human urine samples at room temperature for 5 minutes. Competition resulted in the displacement of some portion of the anti-benzoylecgonine antibody conjugated to HRP. The assay solution consisted of ferrocenecarboxylic acid and hydrogen peroxide. Both concentrations were fixed at 0.5 mM. Silver wire and platinum were used as reference and counter electrodes respectively. Three electrode micro-cells were used with either 5 mL or 20 μl volume. The amount of anti-benzoylecgonine antibody conjugated to HRP displacement in the human urine sample was determined to be proportional to the concentration of free benzoylecgonine in the sample.

Figure 21:
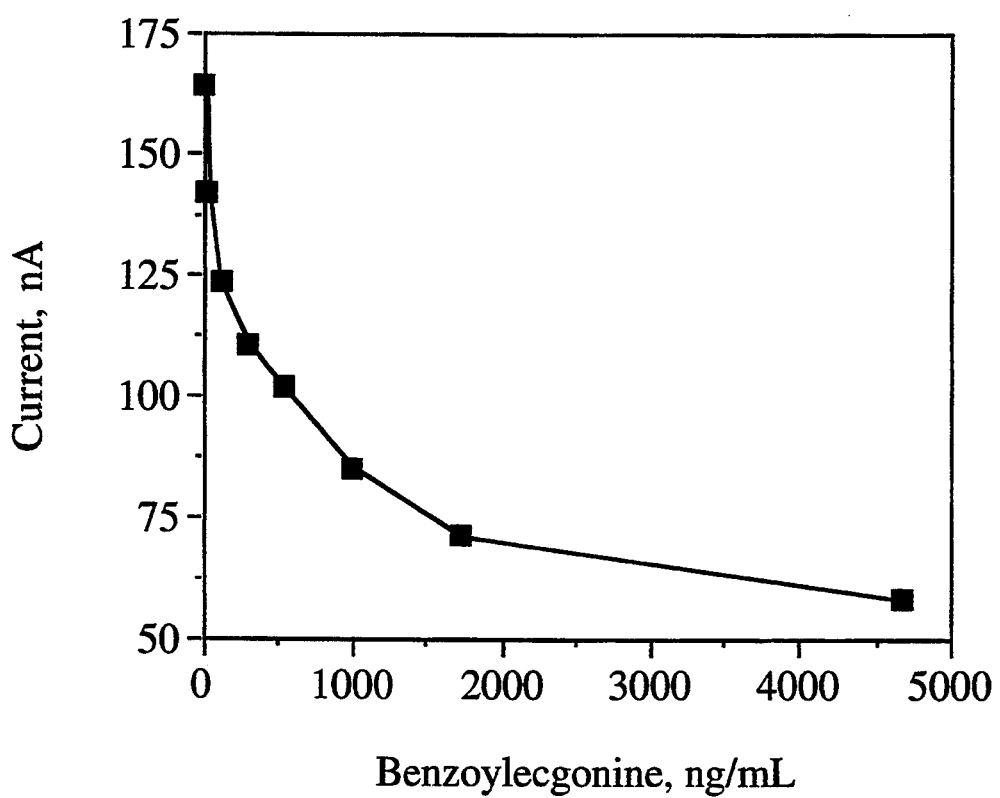
FIG. 21 shows the electroimmunochemical response of benzoylecgonine in a 75% human urine sample.

FIG. 21 shows the electro-immunosensor response to benzoylecgonine concentrations in the human urine sample. Catalytic current of the HRP enzyme decreases with increasing benzoylecgonine concentrations up to 300 ng benzoylecgonine/mL. This assay proved the feasibility of the proposed electro-immunosensor to detect drug metabolites in human urine samples.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques and/or compositions employed herein.

Bushway, R. J., Perkins, B., Savage, S. A., Lekousi, S. L., and Ferguson, B. S. (1989) "Determination of Atrazine Residues in Water and Soil by Enzyme Immunoassay". Bull. Environ. Contam. Toxicol., 40, 647–654.

Bushway, R. J., Perkins, B., Savage, S. A., Lekousi, S. L. and Ferguson, B. S. (1989) "Determination of Atrazine Residues in Food by Enzyme Immunoassay". Bull. Environ. Contam. Toxicol. 42, 899–904.

Karu, A. E., Harrison, R. O., Schmidt, D. J., Clarkson, C. E., Grassman, J., Goodrow, M. H., Lucas, A., Hammock, B. D., Van Emon, J. M., and White, R. J. (1991) "Monoclonal Immunoassay of Triazine Herbicides." in Immunoassays for Trace Chemical Analysis, ACS Symposium Series 451, Vanderlaan, M., Stanker, L. H., Watkins, B. E. and Roberts, D. W., Eds., Washington, DC, Chapter 6.

Monroe, D. (1990) "Amperometric Immunoassays". Critical Reviews in Clinical Laboratory Sciences. 28(1), 1–18.

O'Daly, J. P., Zhao, J., Brown, P. A. and Henkens, R. W. (1992) "Electrochemical enzyme immunoassay for detection of toxic substances" Enzyme Microb. Technol. 14, 299–302.

Vanderlaan, M., Watkins, B. E. and Stanker, L. H. (Dec. 17–22, 1989) The 1989 International Chemical Congress of Pacific Basin Societies, Honolulu, Hi.

Harlow and Lane (1991) Antibodies: A Laboratory Handbook, Cold Spring Harbor Laboratory, Cold Spring Harbor, N.Y.

U.S. Pat. No. 5,217,594

The Cold Spring Harbor Manual for Hybridoma Development

What is claimed is:

1. An electro-immunosensor comprising an electrode on which is deposited a colloidal gold adsorbed anti-analyte antibody bound to an enzyme/analyte conjugate.

2. The electro-immunosensor of claim 1 further comprising treating the colloidal gold with a coating material.

3. The electro-immunosensor of claim 2 wherein the coating material is a protein.

4. The electro-immunosensor of claim 3 wherein the protein is covalently linked or adsorbed to the anti-analyte antibody.

5. The electro-immunosensor of claim 3 wherein the protein is protein A, bovine serum albumin, protein G or avidin.

6. An electrochemical enzyme-linked immunoassay comprising:
   (a) contacting a sample suspected of containing an analyte with an electrode on which is deposited a colloidal gold adsorbed anti-analyte antibody bound to a redox-enzyme/analyte conjugate; and
   (b) determining catalytic current decrease in the presence of a substrate of the redox enzyme when the electrode is coupled with a reference electrode wherein said decrease is related to the level of analyte present in the sample.

7. The immunoassay of claim 6 further including a mediator that enhances electron transfer between the immobilized redox enzyme and the electrode surface.

8. The immunoassay of claim 7 wherein the mediator is ferrocene or a ferrocene derivative.

9. The immunoassay of claim 7 wherein the mediator is immobilized on the electrode surface.

10. The immunoassay of claim 6 wherein the analyte is selected from a group consisting of benzenoids, polynuclear hydrocarbons, nitrogen heterocyclics, sulfur heterocyclics, oxygen heterocyclics, alkane, alkene, alkyne hydrocarbons and polypeptides.

11. The immunoassay of claim 10 wherein the nitrogen heterocycle is a triazine heterocyclic.

12. The immunoassay of claim 11 wherein the triazine heterocyclic is atrazine.

13. The immunoassay of claim 6 wherein the antibody is monoclonal or polyclonal.

14. The immunoassay of claim 6 wherein the redox enzyme is horseradish peroxidase.

15. The immunoassay of claim 14 wherein catalytic current is determined in the presence of a fixed concentration of $H_2O_2$.

16. The immunoassay of claim 15 wherein the $H_2O_2$ concentration is between about 0.2 to about 0.8 mM.

17. A dual site electro immunoassay for analyte determination, comprising:
   contacting a sample suspected of containing an analyte with an electro immunosensor comprising an electrode on which is deposited a colloidal gold adsorbed anti-analyte antibody having specificity for the analyte;
   incubating the sample with a redox enzyme/antibody conjugate wherein the antibody conjugated with the enzyme is specific for the analyte and lacks cross-reactivity with said surface bound antibody; and
   determining an electrochemical response generated from binding of the enzyme/antibody conjugate with the surface bound analyte when the electro immunobiosensor is coupled with a reference electrode wherein the response is a measure of the amount of analyte present in the sample.

18. The immunoassay of claim 17 wherein the analyte is luteinizing hormone or follicle stimulating hormone.

19. The immunoassay of claim 17 wherein the redox enzyme is horseradish peroxidase.

20. An electro-immunosensor comprising:
   (a) a first anti-analyte antibody bound to protein-coated colloidal gold deposited on an electrode surface;
   (b) a second anti-analyte antibody bound to protein-coated colloidal gold deposited on the electrode surface; wherein the first anti-analyte antibody is specific for an analyte which is different from a second analyte and non cross-reactive with the second anti-analyte antibody;
   (c) a first conjugate comprising a first redox enzyme bonded to a separate sample of said anti-analyte antibody; and
   (d) a second conjugate comprising a second redox enzyme bonded to a separate sample of said anti-analyte antibody.

21. The electro-immunosensor of claim 20 wherein the protein is protein A.

22. The electro-immunosensor of claim 20 wherein the first anti-analyte antibody and second anti-analyte antibody are specific for polypeptides.

23. The electro-immunosensor of claim 20 wherein the first anti-analyte antibody is specific for luteinizing hormone.

24. The electro-immunosensor of claim 20 wherein the second anti-analyte antibody is specific for follicle stimulating hormone.

25. The electro-immunosensor of claim 20 wherein the first enzyme is a peroxidase.

26. The electro-immunosensor of claim 20 wherein the first enzyme is horseradish peroxidase.

27. The electro-immunosensor of claim 20 wherein the second enzyme is an oxidase.

28. The electro-immunosensor of claim 27 wherein the second enzyme is glucose oxidase.

29. A dual-analyte electro immunoassay, comprising:
   (a) contacting a sample suspected of containing a first analyte and a second analyte with an electro immunosensor comprising an electrode on which is deposited two colloidal gold adsorbed anti-analyte antibodies each having specificity for said first analyte or said second analyte wherein each analyte binds with its specific antibody to form an analyte/antibody complex;
   (b) incubating the bound analyte/antibody complexes with a first and a second redox enzyme/antibody conjugate wherein one conjugate is a first enzyme bound to an antibody specific for the first analyte that lacks cross reactivity with the first surface bound antibody and the other enzyme conjugate is a second antibody specific for the second analyte that lacks cross reactivity with the second surface bound antibody; and
   (c) measuring an electrochemical response generated from binding of the first and second enzyme-conjugated antibodies with the surface bound first or second analyte/antibody complex when the electro-immunosensor is coupled with a reference electrode to provide a measure of the amount of first or second analyte present in the sample.

30. The electro immunoassay of claim 29 wherein the first analyte is follicle stimulating hormone and the second analyte is luteinizing hormone.

31. The electro immunoassay of claim 29 wherein the antibody is monoclonal or polyclonal.

32. The electro immunoassay of claim 29 wherein the first or second enzyme is a redox enzyme.

33. The electro immunoassay of claim 32 wherein the first and second enzymes are redox enzymes.

34. The electro immunoassay of claim 32 or claim 33 wherein the enzyme is a peroxidase.

35. The electro immunoassay of claim 32 wherein the first enzyme is an oxidase and the second enzyme is a peroxidase.

36. The electro immunoassay of claim 35 wherein the first enzyme is glucose oxidase and the second enzyme is horseradish peroxidase.

37. A single-step electrochemical enzyme-linked immunoassay to detect subnanogram or picogram levels of an organic nitrogen compound in an aqueous sample, comprising contacting a sample suspected of containing said compound with the electrochemical immunosensor of claim I wherein the analyte/enzyme is said nitrogen compound bound to horseradish peroxidase and determining catalytic current decrease in the presence of $H_2O_2$ when the immunosensor is coupled with a reference electrode.

38. The assay of claim 37 wherein the organic nitrogen compound is dinitrophenol.

39. The assay of claim 37 wherein the organic nitrogen compound is atrazine.

40. A method for preparing an electrochemical enzyme immunoassay sensor for determining subnanogram or picogram levels of an immunogenic analyte comprising:
(a) immobilizing on colloidal gold an antibody that specifically reacts with an analyte;
(b) depositing the immobilized antibody on an electrode surface;
(c) separately immobilizing a peroxidase enzyme conjugate on colloidal gold wherein the peroxidase enzyme conjugate is formed between a peroxidase enzyme and the analyte; and
(d) incubating the peroxidase enzyme/analyte conjugate with the electrode surface deposited antibody to form an antibody/peroxidase/conjugate complex.

41. An electro immunosensor comprising an electrode on which is surface-deposited protein-coated colloidal gold bound to an analyte wherein the analyte is bound to an anti-analyte antibody/redox enzyme conjugate.

42. The electro immunosensor of claim 41 wherein the protein is protein A.

43. The electro-immunosensor of claim 1 or claim 20 or claim 41 wherein the electrode is a screen printed carbon black electrode.

44. A kit comprising the electro-immunosensor of claim 1 or claim 20 or claim 41.

45. A single-step electro immunoassay for determining level of an analyte, comprising:
(a) contacting the electro immunosensor of claim 41 with a substrate of the redox enzyme and a sample suspected of containing an analyte; and
(b) amperometrically determining current decrease in the presence of the redox enzyme substrate wherein the current decrease is directly proportional to the level of the analyte.

46. The immunoassay of claim 45 wherein the analyte is benzoylecgonine.

47. The electro immunoassay of claim 45 wherein the redox enzyme is horseradish peroxidase.

* * * * *